United States Patent
Andrews et al.

(10) Patent No.: US 11,169,037 B2
(45) Date of Patent: Nov. 9, 2021

(54) PRISM-COUPLING STRESS METER WITH WIDE METROLOGY PROCESS WINDOW

(71) Applicant: CORNING INCORPORATED, Corning, NY (US)

(72) Inventors: Ryan Claude Andrews, Elmira, NY (US); Chai Hsin Kuang, Taipei (TW); Rostislav Vatchev Roussev, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 16/921,107

(22) Filed: Jul. 6, 2020

(65) Prior Publication Data

US 2020/0333200 A1    Oct. 22, 2020

Related U.S. Application Data

(62) Division of application No. 16/371,517, filed on Apr. 1, 2019, now Pat. No. 10,732,059.
(Continued)

(51) Int. Cl.
*G01B 11/16* (2006.01)
*G01L 1/24* (2006.01)
(Continued)

(52) U.S. Cl.
CPC ............... *G01L 1/24* (2013.01); *G01J 3/447* (2013.01); *G01N 21/23* (2013.01); *G01N 21/43* (2013.01); *G01N 33/386* (2013.01)

(58) Field of Classification Search
CPC ........ G01L 1/241; G01N 21/21; G01N 21/23; G01B 11/18; G01B 11/16
(Continued)

(56) References Cited

U.S. PATENT DOCUMENTS

| 4,152,045 A | 5/1979 | Hammer |
| 8,957,374 B2 | 2/2015 | Liu et al. |

(Continued)

FOREIGN PATENT DOCUMENTS

| CN | 204535899 U | 8/2015 |
| EP | 2437047 A2 | 4/2012 |

(Continued)

OTHER PUBLICATIONS

Chen et al.; "Recovery of Refractive Index Profiles of Planar Graded-Index Waveguides From Measured Mode Indices: An Iteration Method," J. Opt. Soc. Am. A, vol. 9, No. 8, Aug. 1992.
(Continued)

*Primary Examiner* — Md M Rahman
(74) *Attorney, Agent, or Firm* — Kevin M. Johnson

(57) ABSTRACT

The prism-coupling systems and methods include using a prism-coupling system to collect initial TM and TE mode spectra of a chemically strengthened article having a refractive index profile with a near-surface spike region and a deep region. The initial TM and TE mode spectra are examined to see if they fall within a preferred measurement window that can produce an accurate estimate of the knee stress to within a select tolerance. If not, then measurement configuration of the prism-coupling system is changed and new TM and TE mode spectra are collected. This process is repeated until the new TM and TE mode spectra fall within the preferred measurement window. The new TM and TE mode spectra are then used to determine the knee stress. Changing the measurement configuration can include changing at least one of the measurement wavelength, interfacing fluid thickness and interfacing fluid refractive index.

24 Claims, 11 Drawing Sheets

Related U.S. Application Data

(60) Provisional application No. 62/692,233, filed on Jun. 29, 2018, provisional application No. 62/651,442, filed on Apr. 2, 2018.

(51) Int. Cl.
  *G01J 3/447* (2006.01)
  *G01N 33/38* (2006.01)
  *G01N 21/23* (2006.01)
  *G01N 21/43* (2006.01)

(58) Field of Classification Search
  USPC .......................................................... 356/35
  See application file for complete search history.

(56) References Cited

U.S. PATENT DOCUMENTS

| | | | |
|---|---|---|---|
| 9,109,881 | B2 | 8/2015 | Roussev et al. |
| 9,140,543 | B1 | 9/2015 | Allan et al. |
| 9,261,429 | B2 | 2/2016 | Li et al. |
| 9,442,028 | B2 | 9/2016 | Roussev et al. |
| 9,534,981 | B2 | 1/2017 | Roussev et al. |
| 9,696,207 | B2 | 7/2017 | Roussev et al. |
| 9,897,574 | B2 | 2/2018 | Andrews et al. |
| 10,180,416 | B2 | 1/2019 | Roussev et al. |
| 2010/0028607 | A1 | 2/2010 | Lee et al. |
| 2015/0116713 | A1 | 4/2015 | Roussev et al. |
| 2016/0122240 | A1 | 5/2016 | Oram et al. |
| 2016/0356760 | A1 | 12/2016 | Roussev et al. |
| 2018/0306658 | A1 | 10/2018 | Orihara et al. |
| 2019/0033144 | A1 | 1/2019 | Andrews et al. |

FOREIGN PATENT DOCUMENTS

| | | |
|---|---|---|
| WO | 2016/196748 A1 | 12/2016 |
| WO | 2017/115811 A1 | 7/2017 |
| WO | 2019/023441 A2 | 1/2019 |

OTHER PUBLICATIONS

International Search Report and Written Opinion of the International Searching Authority; PCT/US2019/025113; dated Jun. 28, 2019; 13 Pages; European Patent Office.

Oven et al.; "Use of Multiple Wavelength and/or TE/TM Effective-Refractive-Index Measurements to Reconstruct Refractive-Index Profiles"; IEE Proc. Optoelectronics, vol. 144, No. 4; Aug. 1997; p. 213-219.

Surface Stress Meter FSM-6000 LE Standard/Premium, Nov. 2015.

Valles-Villarreal et al.; "Stress in Copper Ion-Exchanged Glass Waveguides"; Journal of Lightwave Technology; vol. 17, No. 4; Apr. 1990; p. 606-612.

White et al.; "Optical Waveguide Refractive Index Profiles Determined From Measurement of Mode Indices: A Simple Analysis"; Applied Optics; Jan. 1976; vol. 15, No. 1 p. 151-155.

Yang et al., "Long-range surface modes of metal-clad four-layer waveguides", Applied Optics, vol. 25, No. 21, Nov. 1, 1986, p. 3903.

Yang et al.; "Improved Method for Recovering Graded-Index Profile of Isotropic Waveguide by Cubic Spline Function" Optical Engineering; 49 (7) (2010) p. 074602-1-074602-5.

Zhu et al.; "Construction of the Refractive Index Profiled for Few-Mode Planar Optical Waveguides"; Science Direct, Optics Communications 260 (2006) p. 542-547.

Zhurikhina et al.; "Ion-Exhange Characteristics of Sodium-Calcium-Silicate Glass; Calculation From Mode Spectra" ISSN; Technical Physics; 2010; vol. 55, No. 10; p. 1447-1452.

PRISM-COUPLING STRESS METER WITH WIDE METROLOGY PROCESS WINDOW

CROSS-REFERENCE TO RELATED APPLICATIONS

This application is a divisional of U.S. application Ser. No. 16/371,517 filed on Apr. 1, 2019, which claims the benefit of priority of U.S. Provisional Application Ser. No. 62/692,233 filed on Jun. 29, 2018 and U.S. Provisional Application Ser. No. 62/651,442 filed on Apr. 2, 2018, the content of each is relied upon and incorporated herein by reference in their entirety.

FIELD

The present disclosure relates to glass-based ion-exchanged (IOX) articles, and in particular to prism-coupling systems and methods of characterizing stress in glass-based chemically strengthened articles with an extended (i.e., relatively large) measurement process window, wherein the chemically strengthened articles having a refractive index profile that includes a near-surface spike region.

BACKGROUND

Chemically strengthened glass-based articles are formed by subjecting glass-based substrates to a chemical modification to improve at least one strength-related characteristic, such as hardness, resistance to fracture, etc. Chemically strengthened glass-based articles have found particular use as cover glasses for display-based electronic devices, especially hand-held devices such as smart phones and tablets.

In one method, the chemical strengthening is achieved by an ion-exchange (IOX) process whereby ions in the matrix of a glass-based substrate ("native ions" or "substrate ions") are replaced by externally introduced (i.e., replacement or in-diffused) ions, e.g., from a molten bath. The strengthening generally occurs when the replacement ions are larger than the native ions (e.g., $Na^+$ or $Li^+$ ions replaced by $K^+$ ions). The IOX process gives rise to an IOX region in the glass that extends from the article surface into the matrix. The IOX region defines within the matrix a refractive index profile having a depth of layer (DOL) that represents a size, thickness or "deepness" of the IOX region as measured relative to the article surface. The refractive index profile also defines stress-related characteristics, including a stress profile, a surface stress, a depth of compression, a center tension, a birefringence, etc. The refractive index profile can also define in the glass-based article an optical waveguide that supports a number m of guided modes for light of a given wavelength when the refractive index profile meets certain criteria known in the art.

Prism-coupling systems and methods can be used to measure the spectrum of the guided modes of the planar optical waveguide formed in the glass-based IOX article to characterize one or more properties of the IOX region, such as the refractive index profile and the aforementioned stress-related characteristics. This technique has been used to measure properties of glass-based IOX articles used for a variety of applications, such as for chemically strengthened covers for displays (e.g., for smart phones). Such measurements are used for quality control purposes to ensure that the IOX region has the intended characteristics and falls within the select design tolerances for each of the selected characteristics for the given application.

While prism-coupling systems and methods can be used for many types of conventional glass-based IOX articles, such methods do not work as well and sometimes do not work at all on certain glass-based IOX articles. For example, certain types of IOX glass-based articles are actual dual IOX (DIOX) glass-based articles formed by first and second ion diffusions that give rise to a two-part profile. The first part (first region) is immediately adjacent the substrate surface and has a relatively steep slope, while the second segment (second region) extends deeper into the substrate but has a relatively shallow slope. The first region is referred to as the spike region or just "spike," while the second region is referred to as the deep region. The optical waveguide is defined by both the spike region and the deep region.

Such two-region profiles result in a relatively large spacing between low-order modes, which have a relatively high effective index, and a very small spacing between high-order modes, which have a relatively low effective index close to the critical angle, which defines the boundary or transition between total-internal reflection (TIR) for guided modes and non-TIR for so-called leaky modes. In a mode spectrum, the critical angle can also be called the "critical angle transition" for convenience. It can happen that a guided mode can travel only in the spike region of the optical waveguide. A guided or leaky mode traveling only in the spike region makes it difficult if not impossible to distinguish between light that is guided only in the spike region and light that is guided in the deep region.

Determining the precise location of the critical angle from the mode spectrum for a glass-based IOX article having a two-region profile is problematic because guided modes that reside close to the critical angle distort the intensity profile at the critical angle transition. This in turn distorts the calculation of the fractional number of mode fringes, and hence the calculation of the depth of the spike region and stress-related parameters, including the calculation of the compressive stress at the bottom of the spike region, which is referred to as the "knee stress" and is denoted $CS_k$.

As it turns out, the knee stress $CS_k$ is an important property of a glass-based IOX article and its measurement can be used for quality control in large-scale manufacturing of chemically strengthened glass-based articles. Unfortunately, the above-described measurement problems impose severe restrictions when using a prism-coupling system to make measurements of IOX articles for quality control because an accurate estimation of the knee stress $CS_k$ requires that the critical angle transition be accurately established for both the transverse electric (TE) and transverse magnetic (TM) guided modes.

SUMMARY

The methods described herein are directed to optimizing the performance of a prism-coupling system when measuring IOX articles that include a near-surface spike region. The optimization is of the measurement window, and in particular increases the measurement window so that an accurate estimate of at least one stress parameter can be obtained when measuring an IOX article. Example stress-related parameters include the knee stress $CS_k$ and spike depth D1, the center tension CT, the tension-strain energy TSE, and an estimate of frangibility, which relates to the center tension CT and/or to the tension-strain energy TSE.

The prism-coupling systems and methods include using a prism-coupling system to collect initial TM and TE mode spectra of a chemically strengthened article having a refractive index profile with a near-surface spike region and a deep region. The initial TM and TE mode spectra are examined to see if they fall within a preferred measurement window that can produce an accurate estimate of the knee stress to within a select tolerance. If not, then measurement configuration of the prism-coupling system is changed and new TM and TE mode spectra are collected. This process is repeated until the new TM and TE mode spectra fall within the preferred measurement window. The new TM and TE mode spectra are then used to determine the knee stress. Changing the measurement configuration can include changing at least one of the measurement wavelength, interfacing fluid thickness and interfacing fluid refractive index.

The systems and methods disclosed herein also enable a wider fabrication window for fabricating IOX articles, especially those made from Li-based substrates that have a large compression depth. In many cases, the fabrication window in production for lithium-containing aluminosilicate glass-based IOX articles with a near-surface spike region R1 has been limited by the size of the available quality-control measurement window, rather than the range of fabrication conditions and stress profile parameters that allow superior mechanical performance within a preferred range.

The systems and methods disclosed herein also suppress false positive measurements of stress-related characteristics. Conventional measurement systems and methods allow measured IOX articles to pass quality control without having the values of defining features of the stress profile (especially $CS_k$) in a preferred range. This can happen due to inadequacies (loopholes) in the measurement methods and the prism-coupling system configuration when measuring IOX articles having a spike region. These loopholes are related in some cases to the distortions occurring for mode spectra immediately adjacent to the preferred measurement window, while in the case of some indirect methods they involve shifting the process target to achieve a similar birefringence of the highest-order guided mode through a different combination of profile parameters, most often by a combination having smaller $CS_k$, but higher potassium-spike DOL or higher surface CS.

The methods and systems described herein provide a measurement in the preferred measurement window where distortions are minimized, and further the direct knee stress $CS_k$ measured in the preferred measurement window is used to verify that the calibration of the indirect component of the hybrid method is correct.

An embodiment of the disclosure is a method for reducing systematic errors in measurements of the knee stress in chemically strengthened glass-based articles. The method comprises: collecting a first angular coupling spectrum for each of the transverse magnetic (TM) and transverse electric (TE) optical polarization states; evaluating for each of TM and TE optical polarizations whether the angular spectrum obtained by prism coupling is in the preferred measurement window; taking corrective action if at least one of the TM and TE spectra is outside the preferred measurement window; and accepting and finishing the measurement if both the TM and TE spectra are in their respective preferred measurement window.

Another embodiment of the disclosure is an apparatus configured to perform the above-described method. The apparatus comprises a prism-coupling based stress meter equipped to perform measurements using at least two wavelengths, sequentially or simultaneously. The stress meter comprises: a prism that couples light from at least one light source to a sample; a polarizing device that selects TM and TE prism coupling spectra at the measurement wavelength; and a sensor device that captures the TM and TE spectra.

Another embodiment of the disclosure is a method of estimating a knee stress in a chemically strengthened article having a refractive index profile with a near-surface spike region and a deep region that define an optical waveguide in a glass-based substrate, comprising: a) using a prism-coupling system set in an initial measurement configuration, collecting TM and TE mode spectra for the chemically strengthened article; b) examining the TM and TE mode spectra and finding that they do not fall within a preferred measurement window that can produce an accurate estimate of the knee stress to within a select tolerance; c) changing the measurement configuration of the prism-coupling system one or more times and measuring new TM and TE mode spectra until the new TM and TE mode spectra fall within the preferred measurement window; and d) using the new TM and TE mode spectra to determine the knee stress.

Another embodiment of the disclosure is a method of performing a measurement knee stress in chemically strengthened ion-exchanged (IOX) article having a near-surface spike region and a deep region that define an optical waveguide in a glass-based substrate, comprising: a) collecting a first mode spectrum comprising a first transverse magnetic (TM) mode spectrum and a first transverse electric (TE) mode spectrum of the optical waveguide using a prism-coupling system having a coupling prism and placed in a first configuration defined by a first measurement wavelength and a thickness and refractive index of an interfacing fluid that resides at an interface between the coupling prism and the IOX article; b) evaluating the first TM mode spectrum and the first TE mode spectrum and finding that at least one of the TM mode spectrum and the TE mode spectrum resides outside of a preferred measurement window that allows estimating the knee stress to within a select tolerance; c) placing the prism-coupling system in a second configuration by adjusting at least one of the measurement wavelength, the thickness of the interfacing fluid and the refractive index of the interfacing fluid; d) collecting with the prism-coupling system in the second configuration a second mode spectrum comprising a second TM mode spectrum and a second TE mode spectrum of the optical waveguide, wherein the second configuration places the second TM mode spectrum and a second TE mode spectrum within the preferred measurement window; and e) determining the knee stress to within the select tolerance using the second TM mode spectrum and a second TE mode spectrum.

Another embodiment of the disclosure is a prism-coupling system for measuring a stress characteristic of a chemically strengthened ion-exchanged (IOX) article having a near-surface spike region and a deep region formed in a glass-based substrate and that define an optical waveguide, comprising:

a) a coupling prism having an input surface, an output surface and a coupling surface, and wherein the coupling surface interfaces with the waveguide at a substrate upper surface, thereby defining an interface having an interfacing fluid with an interfacing fluid refractive index and a thickness;

b) a vacuum system pneumatically connected to the interface and configured to change an amount of vacuum at the interface;

c) an interfacing fluid supply fluidly connected to the interface and configured to supply one or more interfacing fluids to the interface;

d) a light source system that emits measurement light having a measurement wavelength selectable from multiple different measurement wavelengths, wherein the measurement light illuminates the interface through the input surface of the prism, thereby forming reflected light that exits the output surface of the coupling prism, wherein the reflected light defines a transverse magnetic (TM) mode spectrum and a transverse electric (TE) mode spectrum;

e) a photodetector system arranged to receive the reflected light from the coupling prism and detect the first TM mode spectrum and first TE mode spectrum;

f) a controller configured to perform the acts of:
  a. processing the first TM mode spectrum and the first TE mode spectrum to find that at least one of the first TM mode spectrum and the first TE mode spectrum resides outside of a preferred measurement window that allows estimating the knee stress from the first TM mode spectrum and the first TE mode spectrum to within a select tolerance;
  b. placing the prism-coupling system in a second configuration by adjusting at least one of: i) the measurement wavelength, ii) the thickness of the interfacing fluid and iii) the refractive index of the interfacing fluid;
  c. with the prism-coupling system in the second configuration, collecting a second TM mode spectrum and a second TE mode spectrum, wherein the second configuration places the second TM mode spectrum and a second TE mode spectrum within the preferred measurement window; and
  d. determining the knee stress to within the select tolerance using the second TM mode spectrum and a second TE mode spectrum.

Another embodiment of the disclosure is a prism-coupling system for measuring a stress characteristic of a chemically strengthened ion-exchanged (IOX) article having a near-surface spike region and a deep region formed in a glass-based substrate and that define an optical waveguide, comprising: a coupling prism having an input surface, an output surface and a coupling surface, and wherein the coupling surface interfaces with the waveguide at a substrate upper surface, thereby defining an interface having an interfacing fluid with an interfacing fluid refractive index and a thickness; a light source system configured to emit measurement light having a selectable measurement wavelength, wherein the measurement light illuminates the interface through the input surface of the prism, thereby forming reflected light that exits the output surface of the coupling prism, wherein the reflected light defines a transverse magnetic (TM) mode spectrum and a transverse electric (TE) mode spectrum; a photodetector system arranged to receive the reflected light from the coupling prism and detect an initial TM mode spectrum and an initial TE mode spectrum at an initial measurement wavelength; a controller configured to perform the acts of:

i) processing the initial TM mode spectrum and the initial TE mode spectrum and finding that at least one of the first TM mode spectrum and the first TE mode spectrum resides outside of a preferred measurement window that allows estimating the knee stress from the first TM mode spectrum and the first TE mode spectrum to within a select tolerance;

ii) changing the measurement wavelength of the light source one or more times to the selectable measurement wavelengths and collecting respective one or more new TM mode spectrums and one or more new TE mode spectrums until the new TM mode spectrum and the new TE mode spectrum reside within the preferred measurement window; and iii) determining the knee stress to within the select tolerance using the new TM mode spectrum and the TE mode spectrum that reside within the preferred measurement window.

Additional features and advantages are set forth in the Detailed Description that follows, and in part will be apparent to those skilled in the art from the description or recognized by practicing the embodiments as described in the written description and claims hereof, as well as the appended drawings. It is to be understood that both the foregoing general description and the following Detailed Description are merely exemplary, and are intended to provide an overview or framework to understand the nature and character of the claims.

BRIEF DESCRIPTION OF THE DRAWINGS

The accompanying drawings are included to provide a further understanding, and are incorporated in and constitute a part of this specification. The drawings illustrate one or more embodiment(s), and together with the Detailed Description explain the principles and operation of the various embodiments. As such, the disclosure will become more fully understood from the following Detailed Description, taken in conjunction with the accompanying Figures, in which.

DETAILED DESCRIPTION

Figure 1A:
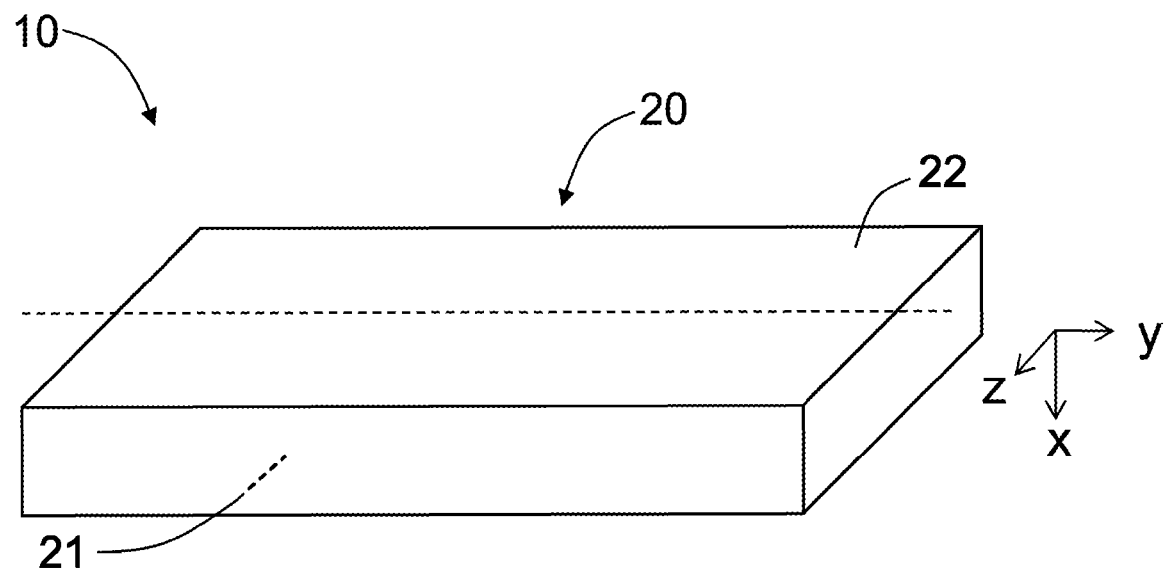
FIG. 1A is an elevated view of an example DIOX glass substrate in the form of a planar substrate.

Reference is now made in detail to various embodiments of the disclosure, examples of which are illustrated in the accompanying drawings. Whenever possible, the same or like reference numbers and symbols are used throughout the drawings to refer to the same or like parts. The drawings are not necessarily to scale, and one skilled in the art will recognize where the drawings have been simplified to illustrate the key aspects of the disclosure.

The acronym IOX can mean either "ion exchange" or "ion exchanged," depending on the context of the discussion. An "IOX article" means an article formed using at least one IOX process. Thus, an article formed by a DIOX process is referred to herein as an IOX article, though it could also be referred to as a DIOX article.

The term "glass based" is used herein to describe a material, article, matrix, substrate, etc., that comprises or consists of either a glass or a glass ceramic.

The compressive stress profile for an IOX article is denoted $CS(x)$ and is also referred to herein as just the stress profile. The surface compressive stress or just "surface stress" for the stress profile is denoted CS and is the value of the compressive stress profile $CS(x)$ for $x=0$, i.e., $CS=CS(0)$, where $x=0$ corresponds to the surface of the IOX article.

The depth of compression DOC is the x distance into the IOX article as measured from the surface of the IOX article to where the compressive stress $CS(x)$ or $CS'(x)$ crosses zero.

The knee stress is denoted $CS_k$ and is the amount of compressive stress at a knee transition point (depth D1) between a spike region (R1) and a deep region (R2), i.e., $CS(D1)=CS_k$.

The spike region R1 has a spike depth from the substrate surface that is denoted both as D1 and $DOL_{sp}$, with the latter also being referred to as the spike depth of layer. The spike region is also referred as a "near-surface spike region" to clarify the distinction with the deep region.

The deep region R2 has a depth D2 which is also denoted as the total depth of layer $DOL_T$ for the total IOX region.

The acronym FWHM means "full-width half maximum."

The terms "preferred measurement window" and "extended measurement window" are synonymous.

The claims as set forth below are incorporated into and constitute part of this detailed description.

Example prism-coupling systems and measurement methods are described for example in: U.S. Application Publication No. 2016/0356760, published Dec. 8, 2016, entitled "METHODS OF CHARACTERIZING ION-EXCHANGED CHEMICALLY STRENGTHENED GLASSES CONTAINING LITHIUM (also published as WO 2016/196748 A1); U.S. Pat. No. 9,897,574, issued Feb. 20, 2018, entitled "METHODS OF CHARACTERIZING ION-EXCHANGED CHEMICALLY STRENGTHENED GLASSES CONTAINING LITHIUM"; and U.S. Application No. 62/538,335, filed Jul. 28, 2017, "METHODS OF IMPROVING THE MEASUREMENT OF KNEE STRESS IN ION-EXCHANGED CHEMICALLY STRENGTHENED GLASSES CONTAINING LITHIUM," and U.S. Pat. No. 9,534,981, issued Jan. 3, 2017, "PRISM-COUPLING SYSTEMS AND METHODS FOR CHARACTERIZING ION-EXCHANGE WAVEGUIDES WITH LARGE DEPTH-OF-LAYER," each of which is incorporated herein by reference in its entirety.

IOX Article

Figure 1B:
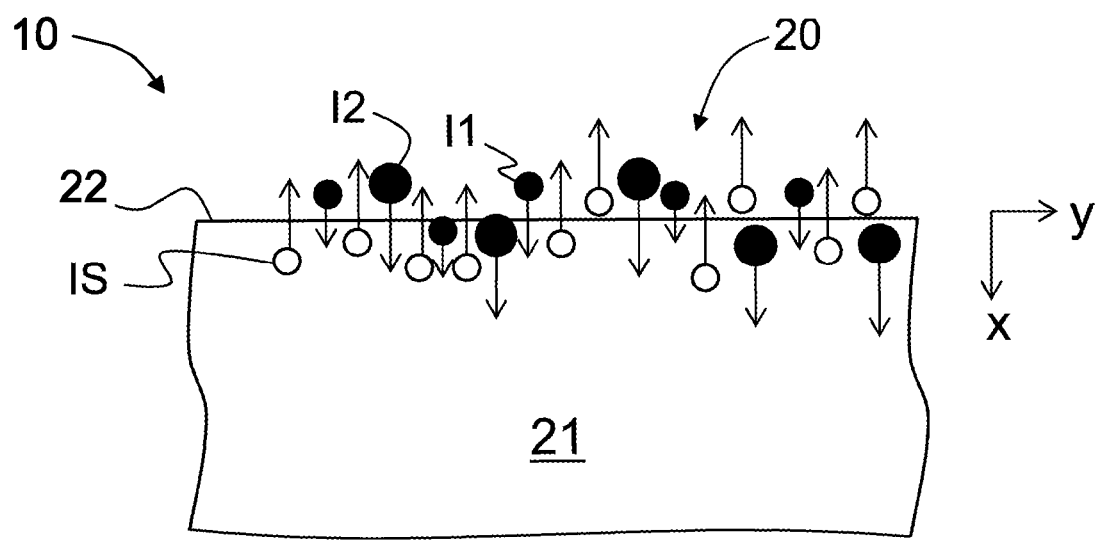
FIG. 1B is a close-up cross-sectional view of the DIOX substrate of FIG. 1A as taken in the x-y plane and that illustrates an example DIOX process that takes place across the substrate surface and into the body of the substrate.

FIG. 1A is an elevated view an example IOX article 10. The IOX article 10 comprises a glass-based substrate 20 having a matrix 21 that defines a (top) surface 22, wherein the matrix has a base (bulk) refractive index $n_s$ and a surface refractive index no. FIG. 1B is a close-up cross-sectional view of the IOX article 10 as taken in the x-y plane and illustrates an example DIOX process that takes place across the surface 22 and into the matrix 21 in the x-direction to form the example IOX article.

Figure 1C:
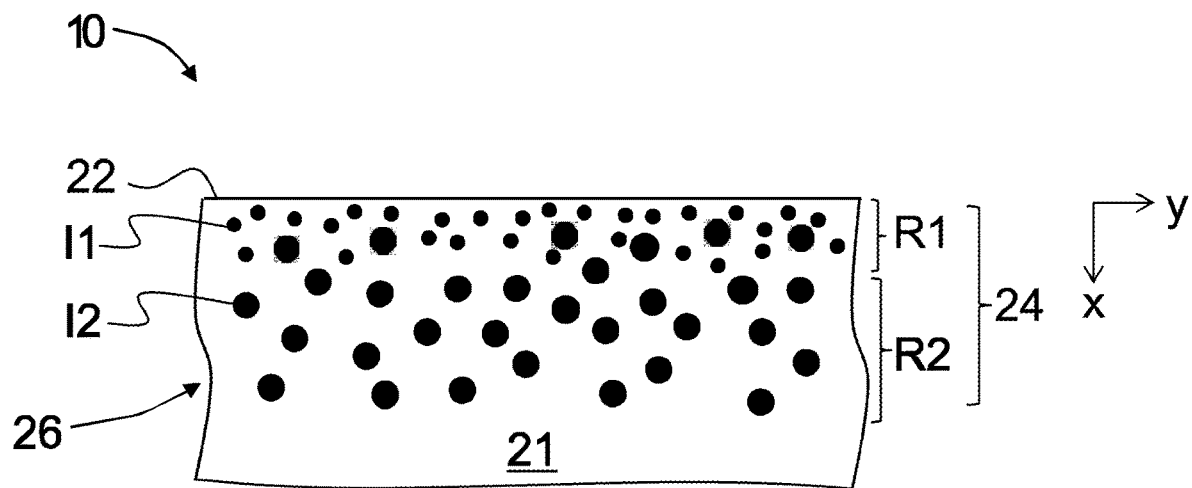
FIG. 1C schematically illustrates the result of the DIOX process that forms the DIOX substrate.

The substrate 20 includes in the matrix 21 substrate ions IS, which exchange for first ions I1 and second ions I2. The first and second ions I1 and I2 can be introduced into the matrix 21 either sequentially or concurrently using known techniques. For example, second ions I2 can be $K^+$ ions introduced via a $KNO_3$ bath for strengthening, prior to introducing first ions I1 that can be $Ag^+$ ions introduced via a $AgNO_3$-containing bath to add an anti-microbial property adjacent surface 22. The circles in FIG. 1B that represent ions I1 and I2 are used for schematic illustration only, and their relative sizes do not necessarily represent any actual relationship between the sizes of the actual ions participating in the ion exchange. FIG. 1C schematically illustrates the result of a DIOX process that forms the IOX article 10, wherein the substrate ions IS are omitted in FIG. 1C for ease of illustration and are understood as constituting the matrix 21. The DIOX process forms an IOX region 24 that includes a near-surface spike region R1 and a deep region R2, as explained below. The IOX region 24 defines an optical waveguide 26.

In addition, ions I1 may be present in significant numbers in both regions R1 and R2 (see FIG. 2, introduced and discussed below) as may be ions of type I2. Even with a one-step ion-exchange process it is possible to observe the formation of two IOX regions R1 and R2, with significant differences in the relative concentrations of ions I1 and I2. In an example, using an ion exchange of Na-containing or Li-containing glass in a bath containing a mixture of $KNO_3$ and $AgNO_3$, it is possible to obtain the spike region R1 with significant concentrations of both $Ag^+$ and $K^+$, and the deep region R2 also with significant concentrations of $Ag^+$ and $K^+$, but the relative concentration of $Ag^+$ with respect to $K^+$ may be significantly larger in the spike region R1 than in the deep region R2.

Figure 2:
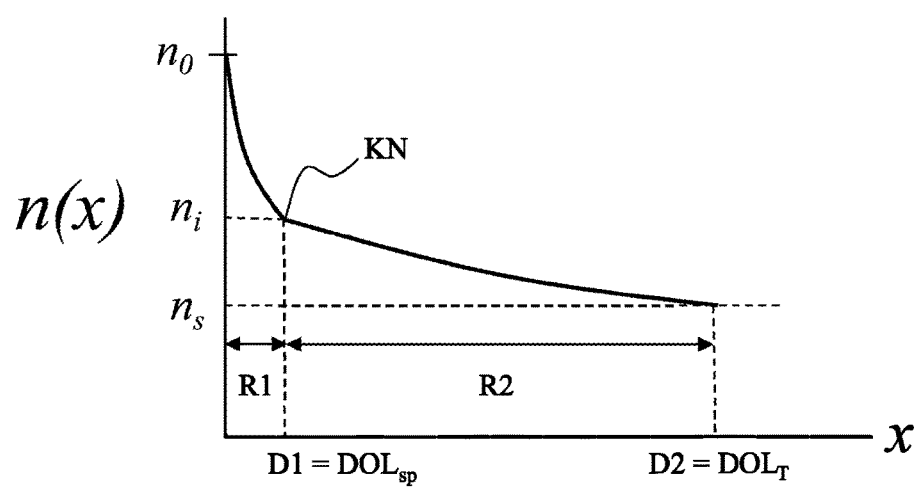
FIG. 2 is a representation of an example refractive index profile $n(\lambda)$ for the DIOX substrate illustrated in FIG. 1C, showing the spike region, the deep region, and the knee at the transition between the two regions.

FIG. 2 is a representation of an example refractive index profile n(x) for an example IOX article 10, such as illustrated in FIG. 1C, and showing the spike region R1 associated with the shallower ion-exchange (ions I1) and that has a depth D1 (or $DOL_{sp}$) into the matrix 21. The deep region R2 associated with the deeper ion-exchange (ions I2) and has a depth D2 that defines the total depth-of-layer ($DOL_T$). In an example, the total $DOL_T$ is at least 50 μm and further in an example can be as large as 150 μm or 200 μm. The transition between the spike region R1 and the deep region R2 defines a knee KN in the refractive index profile n(x) and also in the corresponding stress profile CS(x), as described below.

The deep region R2 may be produced in practice prior to the spike region R1. The spike region R1 is immediately adjacent the substrate surface 22 and is relatively steep and shallow (e.g., D1 may be on the order of microns), whereas the deep region R2 is less steep and extends relatively deep into the substrate to the aforementioned depth D2. In an example, the spike region R1 has a maximum refractive index no at substrate surface 22 and steeply tapers off to an intermediate index $n_i$ (which could also be called the "knee index"), while the deep region R2 tapers more gradually from the intermediate index down to the substrate (bulk) refractive index $n_s$. It is emphasized here that other IOX processes can result in a steep and shallow near-surface refractive index change and that a DIOX process is discussed here by way of illustration.

In some examples, the IOX article 10 is frangible while in other examples, it is non-frangible, according to the frangibility criteria set forth below.

Prism-Coupling System

Figure 3A:
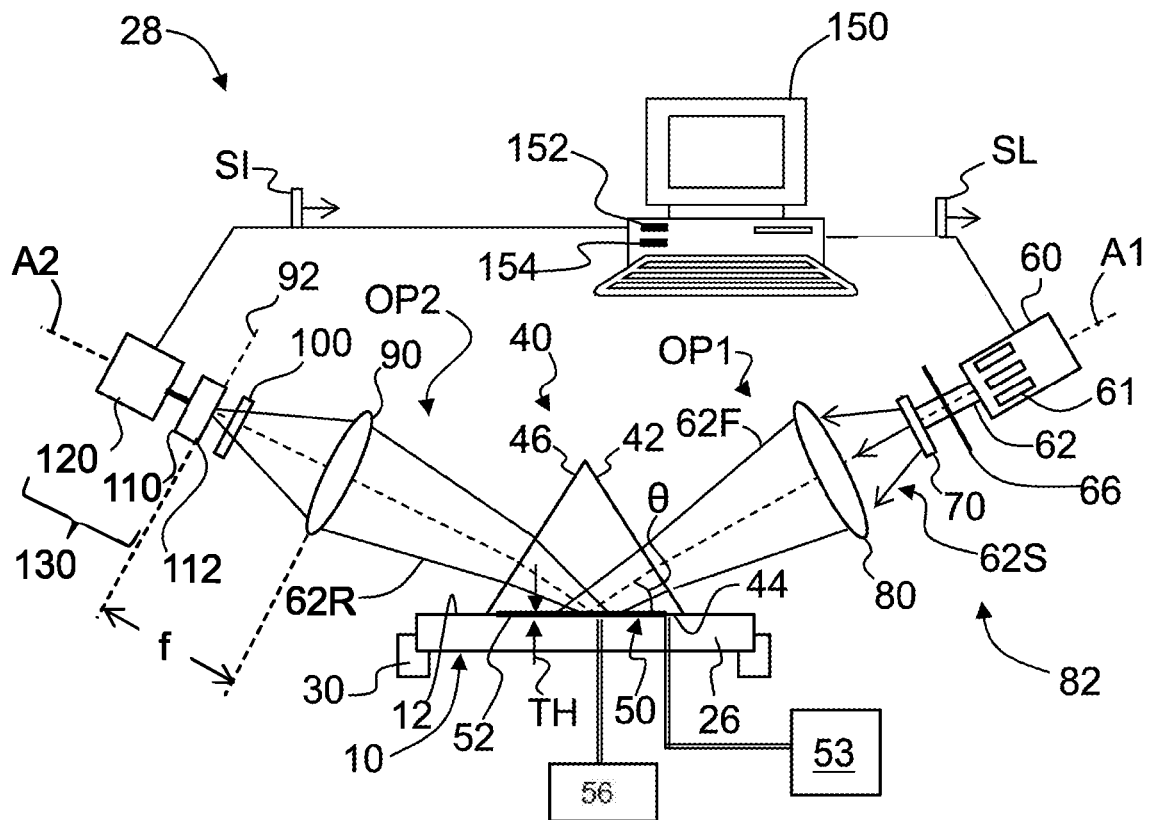
FIG. 3A is a schematic diagram of an example prism-coupling system according to the disclosure and that is used to measure IOX articles using the methods disclosed herein.

FIG. 3A is a schematic diagram of an example prism-coupling system 28 that can be used to carry out aspects of the methods disclosed herein. The prism coupling methods using the prism-coupling system 28 are non-destructive. This feature is particularly useful for measuring frangible IOX articles for research and development purposes and for quality control in manufacturing.

The prism-coupling system 28 includes a support stage 30 configured to operably support the IOX article 10. The prism-coupling system 28 also includes a coupling prism 40 that has an input surface 42, a coupling surface 44 and an output surface 46. The coupling prism 40 has a refractive index $n_p$>$n_0$. The coupling prism 40 is interfaced with the IOX article 10 being measured by bringing coupling-prism coupling surface 44 and the surface 22 into optical contact, thereby defining an interface 50 that in an example can include an interfacing (or index-matching) fluid 52 having a thickness TH. In an example, the prism-coupling system 28 includes an interfacing fluid supply 53 fluidly connected to the interface 50 to supply the interfacing fluid 52 to the interface. This configuration also allows for different interfacing fluids 52 with different refractive indices to be deployed. Thus, in an example, the refractive index of the interfacing fluid 52 can be changed by operation of the interfacing fluid supply 53 to add a higher-index or lower-index interfacing fluid. In an example, the interfacing fluid supply 53 is operably connected to and controlled by the controller 150.

In an exemplary measurement, a vacuum system 56 pneumatically connected to the interface 50 can be used to control the thickness TH by changing the amount of vacuum at the interface. In an example, the vacuum system is operably connected to and controlled by the controller 150.

The prism-coupling system 28 includes input and output optical axes A1 and A2 that respectively pass through the input and output surfaces 42 and 46 of the coupling prism 40 to generally converge at the interface 50 after accounting for refraction at the prism/air interfaces. The prism-coupling system 28 includes, in order along the input optical axis A1, a light source 60 that emits measuring light 62 of wavelength λ, an optional optical filter 66 that may be alternatively included in the detector path on axis A2, an optional light-scattering element 70 that forms scattered light 62S, and an optional focusing optical system 80 that forms focused (measuring) light 62F, as explained below. Thus, in an example of the prism-coupling system 28, there are no optical elements between light source 60 and prism input surface 42. The components from the light source 60 to the focusing optical system 80 constitute an illumination system 82.

The prism-coupling system 28 also includes, in order along the output optical axis A2 from the coupling prism 40, a collection optical system 90 having a focal plane 92 and a focal length f and that receives reflected light 62R as explained below, a TM/TE polarizer 100, and a photodetector system 130.

The input optical axis A1 defines the center of an input optical path OP1 between the light source 60 and the coupling surface 44. The input optical axis A1 also defines a coupling angle θ with respect to the surface 12 of the IOX article 10 being measured.

The output optical axis A2 defines the center of an output optical path OP2 between the coupling surface 44 and the photodetector system 130. Note that the input and output optical axes A1 and A2 may be bent at the input and output surfaces 42 and 46, respectively, due to refraction. They may also be broken into sub-paths by inserting mirrors (not shown) into the input and output optical paths OP1 and/or OP2.

Figure 3B:
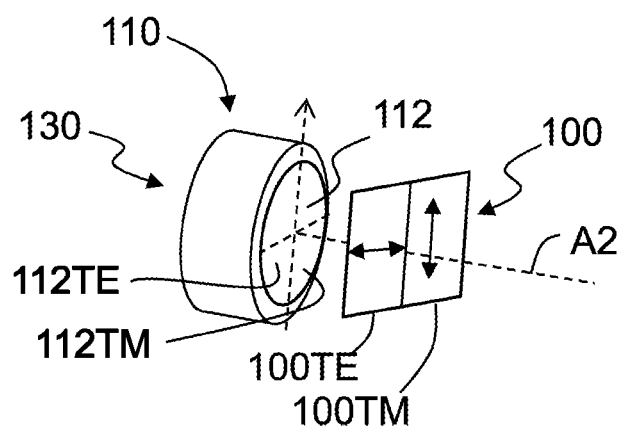
FIG. 3B is a close-up view of the photodetector system of the prism-coupling system of FIG. 3A.

In an example, the photodetector system 130 includes a detector (camera) 110 and a frame grabber 120. In other embodiments discussed below, the photodetector system 130 includes a CMOS or CCD camera. FIG. 3B is a close-up elevated view of the TM/TE polarizer 100 and the detector 110 of the photodetector system 130. In an example, the TM/TE polarizer includes a TM section 100TM and a TE section 100TE. The photodetector system 130 includes a photosensitive surface 112.

The photosensitive surface 112 resides in the focal plane 92 of the collecting optical system 90, with the photosensitive surface being generally perpendicular to the output optical axis A2. This serves to convert the angular distribution of the reflected light 62R exiting the coupling prism output surface 46 to a transverse spatial distribution of light at the sensor plane of the camera 110. In an example embodiment, the photosensitive surface 112 comprises pixels, i.e., the detector 110 is a digital detector, e.g., a digital camera.

Figure 3C:
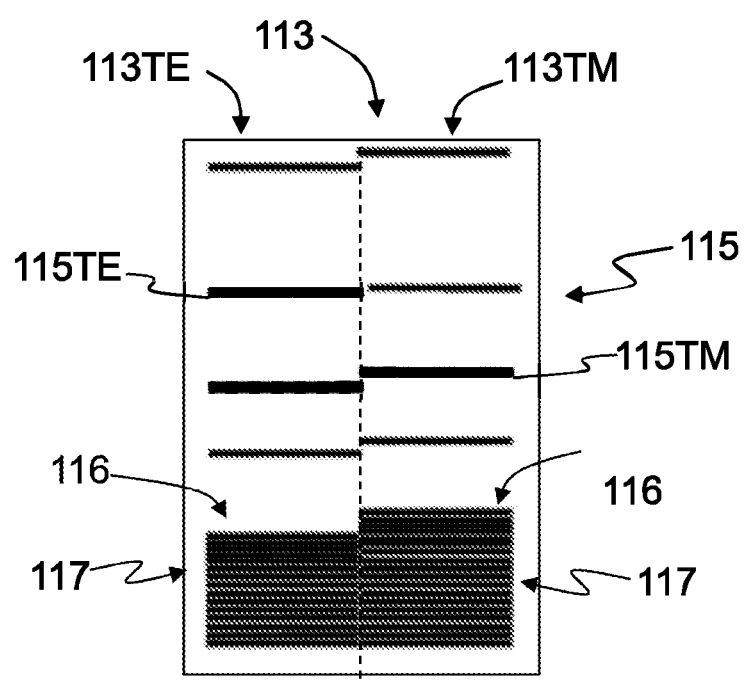
FIG. 3C is a schematic representation of a mode spectrum that includes TM and TE mode spectra as captured by the photodetector system of FIG. 3B.

Splitting the photosensitive surface 112 into TE and TM sections 112TE and 112TM as shown in FIG. 3B allows for the simultaneous recording of digital images of the angular reflection spectrum (mode spectrum) 113, which includes the individual TE and TM mode spectra 113TE and 113TM for the TE and TM polarizations of the reflected light 62R. This simultaneous detection eliminates a source of measurement noise that could arise from making the TE and TM measurements at different times, given that system parameters can drift with time. FIG. 3C is a schematic representation of a mode spectrum 113 as captured by the photodetector system 130. The mode spectrum 113 has total-internal-reflection (TIR) section 115 associated with guided modes and a non-TIR section 117 associated with radiation modes and leaky modes. A transition 116 between the TIR section 115 and the non-TIR section 117 defines a critical angle and is referred to as the critical angle transition 116.

The TM mode spectrum 113TM includes mode lines or fringes 115TM while the TE mode spectrum 113TE includes mode lines or fringes 115TE. The mode lines or fringes 115TM and 115TE can either be bright lines or dark lines, depending on the configuration of the prism-coupling system 28. In FIG. 3C, the mode lines or fringes 115TM and 115TE are shown as dark lines for ease of illustration. In the discussion below, the term "fringes" is used as short-hand for the more formal term "mode lines."

The stress characteristics are calculated based on the difference in positions of the TM and TE fringes 115TM and 115TE in the mode spectrum 113. At least two fringes 115TM for the TM mode spectrum 113TM and at least two fringes 115TE for the TE mode spectrum 113TE are needed to calculate the surface stress CS. Additional fringes are needed to calculate the stress profile CS(x).

With reference again to FIG. 3A, the prism-coupling system 28 includes a controller 150, which is configured to control the operation of the prism-coupling system. The controller 150 is also configured to receive and process from the photodetector system 130 image signals SI representative of captured (detected) TE and TM mode spectra images. The controller 150 includes a processor 152 and a memory unit ("memory") 154. The controller 150 may control the activation and operation of the light source 60 via a light-source control signal SL, and receives and processes image signals SI from the photodetector system 130 (e.g., from the frame grabber 120, as shown). The controller 150 is programmable to perform the functions described herein, including the operation of the prism-coupling system 28 and the aforementioned signal processing of the image signals SI to arrive at a measurement of one or more of the aforementioned stress characteristics of the IOX article 10.

A proper measurement of a stress characteristic of the IOX article 10 conventionally requires that the prism-coupling system 28 couple the focused light 62F into a sufficient number of the guided modes supported by the IOX waveguide 26 so that most if not all of the refractive index profile in the spike region R1 as well as the deep region R2 is sampled so that the measured mode spectrum 113 is complete and accurate, i.e., includes information about the entire IOX region 24 and not just a one part of the IOX region.

When a guided or leaky mode associated with the spike region R1 has an effective index that is close to the critical angle, determining the precise location of the critical angle transition 116 in the mode spectrum 113 can be problematic. This is because the usual location of the maximum slope in the intensity profile can correspond to a slightly different effective index than the actual effective index at the spike depth D1, i.e., at the knee KN formed by the transition between the spike region and the deep region R2 (see FIG. 2). As noted above, the resonance caused by the nearby guided or leaky mode in the effective-index spectrum can cause a significant change in the shape of the intensity distribution in the vicinity of the effective index corresponding to the index at the knee KN. As noted above, this can substantially distort the calculation of the fractional number of TE and TM fringes 115TE and 115TM, and hence of the spike depth D1, and thus the calculation of the knee stress $CS_k$. This is particularly true for Li-based glass substrates 20 that undergo a DIOX process using Na+ and K+ ions to form the IOX article 10.

The above-described calculation distortions impose severe restrictions when using prism-coupling measurements for quality control of IOX articles 10 since an accurate estimation of the knee stress $CS_k$ is only possible in a narrow range of conditions (i.e., a narrow measurement process window) where the critical-angle intensity transition is unperturbed for both the TM and TE polarizations.

Example methods of operating the prism-coupling system 28 to provide a relatively large measurement process window call for configuring the prism-coupling system to change the measurement wavelength λ of the light 62 from the light source 60. In an example shown in FIG. 3A, the light source 60 can configured with individual light-emitting elements 61 each configured to emit a different measurement wavelength λ. Three example measurement wavelengths λ, which can be respectively denoted as λ1, λ2 and λ3 can include 540 nm, 595 nm and 650 nm. In an example, the light-emitting elements 61 comprise at least one of light-emitting diodes and laser diodes. In some embodiments, several light-emitting elements 61 are arranged around a central position such that each light-emitting element 61 is relatively close to a central position, which may lie on the input optical axis A1. In an example, the measurement wavelengths λ fall within the wavelength range from 540 nm to 650 nm.

In a pre-existing one-wavelength illumination system 82, a single light-emitting element 61 can be positioned in a central position on the input optical axis A1. Significant shifts from this central position can be problematic when switching between wavelengths for measurements. In an example, the light-emitting elements 61 can be mounted on a rotatable fixture that positions one of the multiple light-emitting elements 61 onto the input optical axis A1.

Figure 3D:
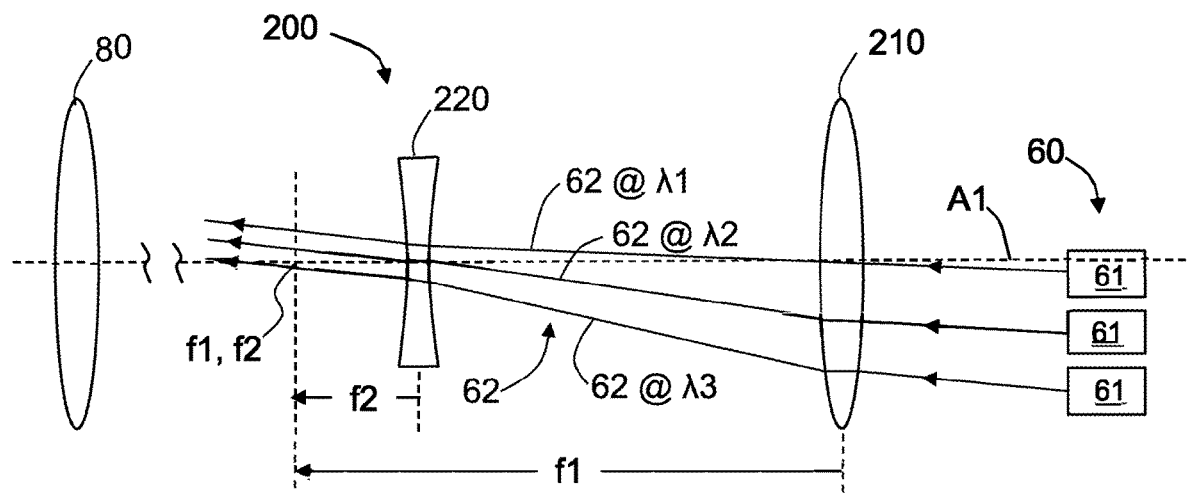
FIG. 3D is a schematic diagram of an example optical system used to direct light from different off-axis light-emitting elements of an example light source.

If the light-emitting elements 61 cannot be brought to within about 2 mm to 3 mm of the optical axis A1 using mechanical means, then optical means can be used. FIG. 3D is a schematic diagram of an example optical system 200 in the form of a reverse telescope. The optical system 200 includes a positive lens 210 of focal length f1 and a negative lens 220 of focal length f2 arranged along the input optical axis A1. The vertical dashed line shows where the focal length f1 and the focal length f2 reside at a common point on the input optical axis.

Three off-axis light-emitting elements 61 are shown that emit light 62 having respective wavelengths λ1, λ2 and λ3. The magnification M of the optical system 200 is given by f2/f1. In an example f2=15 mm and f1=75 mm, for a magnification of 0.2×. This fractional or reduction factor acts to effectively increase the distance to the light source 60 by a factor of nearly 5×, making the light-emitting elements 61 appear closer together from the perspective of the coupling prism location, allowing near-centered illumination for each choice of measurement wavelengths. This is shown in FIG. 3D by the closeness of the three light rays 62 exiting the negative lens 220 as compared to the three light rays exiting the light-emitting elements 61.

Other configurations for optical system 200 can be used to define a suitable amount of reduction magnification. In an example, a light diffuser (e.g., glass plate with abraded scattering surface) can be positioned near the vertical dashed line denoted "f1, f2," where a relatively small bright spot can be formed when any one of the three light-emitting elements 61 is activated.

In a related arrangement, two light-emitting elements were used at each of the three wavelengths, with each pair positioned diametrically around the central position of the light source on the optical axis. This configuration allows for more uniform illumination in the middle of the two-dimensional angular spectrum imaged on the detector (camera) 110 that captures the mode spectrum 113.

In some embodiments, the light-emitting elements 61 may be disposed along a single line. For example, the light-emitting elements 61 may illuminate a diffraction grating (not shown), and the light beam 62 may be controlled with lenses before and after interacting with the diffraction grating, such that a significant fraction of the light is collected and sent to the coupling prism 40. The diffraction grating serves to combine beams emanating from slightly differing neighboring locations and send these beams in a single primary direction toward the prism entrance facet for illuminating the prism-sample interface through the entrance facet. In an example, the diffraction grating may be used in reflection, and may be substantially blazed for the average wavelength of the range of wavelengths utilized for the measurement, such that a very high percentage of the light that is spectrally selected by the diffraction grating is diffracted in the direction of the measurement prism.

In some embodiments, the light-emitting elements 61 may be disposed along a single line, and arranged in sequence from the smallest wavelength to the largest. The light 62 from the light-emitting elements 62 may be passed through an optional lens, and then passed through a high-dispersion prism that combines the light from the multiple light-emitting elements emanating from slightly different locations and send the light along substantially the same optical path connecting the combining dispersive prism with the measurement coupling prism for illuminating the interface 50 for performing a prism-coupling measurements of stress.

In some embodiments, the light source 60 is configured to have a continuously tunable wavelength. In one example, the light source 60 comprises a broadband LED and a tunable filter. In another example, the light source 60 comprises a tunable laser and an optical diffuser for reducing laser speckle. With a tunable filter, the wavelength may be tuned until both the TM and TE mode spectra 113TM and 113TE are found in the preferred measurement window, as described below. Even with a relatively small tuning range of 5% of the central wavelength of the tuning range, a significant increase in the preferred measurement window can be obtained. In an example, a preferred tuning range is 10% of the central measurement wavelength λ.

In some embodiments, the prism-coupling system 28 can include several coupling prisms 40 coupled to different areas of the IOX article. Each coupling prism 40 is configured to be illuminated with a different measurement wavelength λ from the light source 60. Likewise, the reflected light 62R from each coupling prism can be detected by a photodetector system 130 or on a different portion of the light-sensitive surface 112 or by separate photodetector systems.

Measurements can then performed using multiple coupling prisms 40 and using multiple measurement wavelengths λ until at one of the wavelengths the requirements for measurement in the preferred measurement window is satisfied for both TM and TE polarization states. In a similar embodiment, a single wide coupling prism 40 may be contacted to a large area of the IOX article 10. Different locations of the interface 50 may be illuminated at different measurement wavelengths λ, simultaneously or sequentially, with the corresponding mode spectra 113 collected using separate photodetector system 130, or on different portions of the light-sensitive surface 112, which is made sufficiently large to allow for individual measurements.

Measurement Methods Using the Prism-Coupling System

The methods disclosed include different ways of identifying whether a TM or TE mode spectrum 113TM or 113TE is within a preferred (i.e., sufficiently large) measurement window for making an accurate measurement of at least one stress-related property of the IOX article 10 being measured. If either of the TM or TE mode spectrum 113TM or 113TE is not within a preferred measurement window, then the methods include setting the prism-coupling system 28 to a different measurement configuration that allows for both the TM and TE mode spectra 113TM and 113TE to be within the preferred measurement window to obtain a more accurate measure of at least one stress parameter of the IOX article 10. In other words, the method is directed to optimizing the measurement configuration of the prism-coupling system for measuring an IOX article having a spike region R1.

A first method for setting the prism-coupling system 28 to a different measurement configuration includes changing the measurement wavelength λ by a select amount. A second method includes changing at least one of the thickness TH and refractive index $n_f$ of the interfacing fluid 52 at the interface 50. A third method combines the the first and second methods.

Example Method

In a first step of the method, the IOX article 10 is loaded into the prism-coupling system 28 and a first mode spectrum 113 is collected as described above.

In a second step of the method, the first TM and TE spectra 113TM and 113TE are processed to obtain a TM and TE signal of intensity versus position of the respective fringes 115TM and 115TE captured by the photosensitive surface 112 of the photodetector system 130. This is equivalent to the intensity vs. coupling angle θ, which is also equivalent to the intensity vs. effective index $n_{eff}$, as there is a one-to-one relationship between position on the photosensitive surface 112, the coupling angle θ, and the effective index $n_{eff}$ of guided optical modes propagating in the waveguide 26 defined by the IOX region 24 in the IOX article 10.

In a third step, the intensity versus position data from the second step is used to establish whether the first TM and TE mode spectra 113TM and 113TE were obtained (or reside in) a preferred measurement window of the prism-coupling system 28. In one example, this includes determining the fractional portion of the full (real-number) mode count or fringe count for the TM mode spectrum 113TM and the TE mode spectrum 113TE. The full mode count includes an integer portion equal to the number of guided modes for the specific polarization (TM or TE), which is the same as the number of fringes 115TM or 115TE occurring in the TIR section 117 of the respective mode spectra 113TM or 113TE at the measurement wavelength. The number of TM fringes 115TM is $N_{TM}$ while the number of TE fringes 115TE is $N_{TE}$.

Figure 3E:
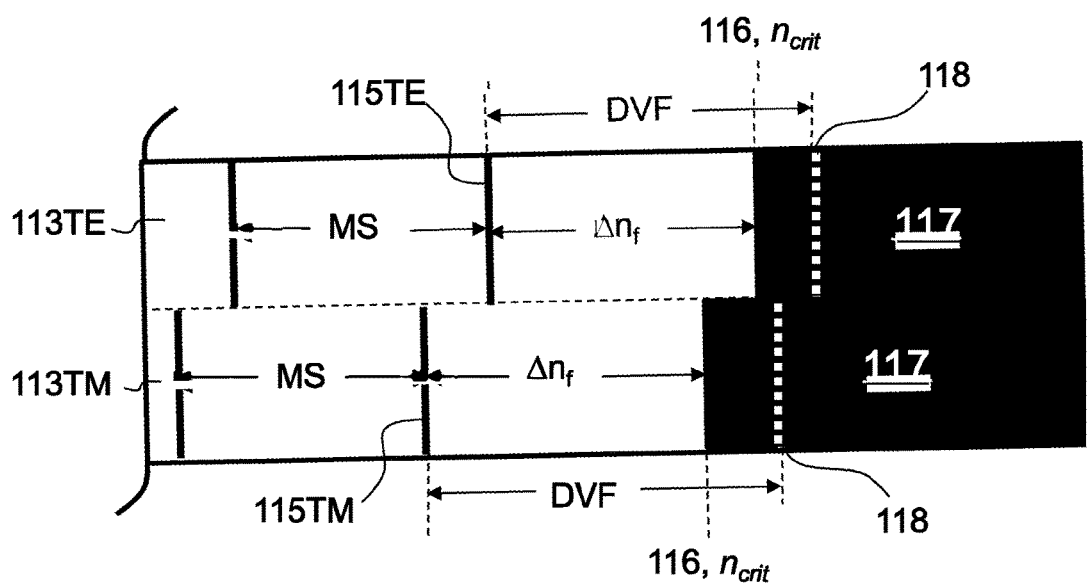
FIG. 3E is a schematic diagram of a portion of an example mode spectrum similar to that of FIG. 3C and illustrating an example method of determining the fractional mode number from the measured mode spectrum for the TE and TM mode spectra.

An aspect of the methods disclosed herein involves determining a fractional portion FP of the number of modes (mode number) for both the TE mode spectrum 113TE and the TM mode spectrum 113TM. FIG. 3E is a schematic diagram of a portion of an example mode spectrum 113 similar to FIG. 3C and illustrating how the fractional portion FP of the mode number for the TE mode spectrum 113TE and the TM mode spectrum 113TM can be determined.

In an example, the fractional portion FP of the mode number is determined by comparing the distance between the last guided mode having the lowest effective index $n_{eff}$, and the effective index $n_{eff}$ corresponding to the critical angle transition 116. For coupling angles θ beyond the critical angle, only part of the incident light 62F is reflected to form reflected light 62R, with the non-reflected portion of the incident light penetrating the IOX article 10 substantially deeper than the spike depth D1 as a leaky mode or a radiation mode.

The effective index $n_{eff}$ corresponding to the critical angle is referred to as the "critical index" and is denoted $n_{crit}$. In some cases, the critical index $n_{crit}$ can equal the substrate refractive index $n_s$. For example, this situation can arise when the IOX article 10 is formed from an Li-containing glass substrate 20 that is chemically strengthened in a bath containing $Na^+$ (e.g., $NaNO_3$).

The distance between the last guided mode and the critical angle $n_{crit}$ corresponds to the difference $\Delta n_f$ in effective index between the index of the last guided mode and the critical index is given by:

$$\Delta n_f = \min(n_{eff}) - n_{crit}$$

where $\min(n_{eff})$ is the smallest of the effective indices of all guided modes for the specific polarization (TM or TE), and $n_{crit}$ is the critical index for the same polarization.

The fractional portion FP of the mode count (i.e., number of fringes) $N_{TM}$ or $N_{TE}$ is found by examining the space between the last guided mode 115TE or 115TM and the critical index $n_{crit}$. In some embodiments, the fractional portion of the TM or TE mode count is determined by comparing $\Delta n_f$ to the expected spacing to the next mode by extrapolating the dependence of effective index on the mode count. In some embodiments, a fit of the dependence of effective index $n_{eff}$ on the mode count can be obtained from the integer-numbered guided modes. The fit is then extrapolated, and a mode number is assigned to the critical angle $n_{crit}$ from the value of the mode count $N_{TM}$ or $N_{TE}$ at which the extrapolated function equates to the measured $n_{crit}$. This same procedure may be performed directly using the position of fringes 115TM or 115TE in the given mode spectrum 113TM or 113TE versus the fringe number, or an angle in the angular spectrum versus fringe number.

One method of determining the fractional portion FP of the fringe count is to consider a virtual fringe 118 that would be the next fringe in the given mode spectrum but for the fact that the critical angle transition 116 cuts off the virtual fringe. This can be accomplished by an extrapolation based the existing fringe spacings. The distance from the last fringe 115TE or 115TM to the corresponding virtual fringe 118 is DVF, so that the fractional portion FP of the mode (fringe) count is $FP = \Delta n_f / DVF$, noting that $\Delta n_f$ and DVF can be different for the TM mode spectrum 113TM and the TE mode spectrum 113TE.

Another method of determining the fractional portion FP of the fringe count is when there are only two or three modes. In this case, one can approximate the distance DVF by the spacing MS between the two modes closest to the TIR-PIR transition, as also shown in FIG. 3E.

In one example, to be within the preferred measurement window, the fractional portion FP of the fringe count $N_{TM}$ or $N_{TE}$ is within a select range. In one example, the range on the fraction portion FP of the fringe count is 0.1 to 0.85. In another example, the fractional portion FP of the fringe count can be greater than 0.15. In another example, the fractional portion FP of the fringe count can be below 0.8, e.g., smaller than 0.75, or smaller than 0.70. Thus, example ranges on FP include 0.15 and 0.75 or 0.15 and 0.70. If the fractional portion FP of at least one of the TM mode spectrum 113M and the TE mode spectrum 113TE is outside of the select range, then the prism-coupling system 28 is set to a different measurement condition that brings the fraction portion FP of the fringe count to within the select range, which in turn allows for determining the at least one stress parameter of the IOX article 10 with better accuracy.

In another example, to be within the preferred measurement window, there can be no guided or a leaky mode close enough to the critical index $n_{crit}$ to substantially alter the shape (intensity profile) of the critical angle transition 116. This is because location of the maximum intensity slope of the critical angle transition 116 is used to determine the stress-related parameters of the IOX article 10. A guided or leaky mode resonance that adversely affects the critical-angle intensity transition in the captured prism-coupling spectrum is referred to herein as an offending resonance or an offending mode.

As utilized herein, an optical propagation mode is referred to as "guided" or "bound" if its effective index is higher than the critical index. As utilized herein, an optical propagation mode is referred to as "leaky" if its effective index is lower than the critical index. A leaky mode produces a transmission resonance when its effective index is relatively close to the critical index, particularly if it is substantially closer to the mode spacing of the last two guided modes, i.e., the two guided modes with the lowest effective index for a particular polarization.

As utilized herein, the "transmission resonance" refers to a dip in the intensity in a given mode spectrum 113TM or 113TE where the intensity would normally monotonically decrease with decreasing effective index for $n_{eff} < n_{crit}$. When the dip in the mode spectrum gets very close to the critical-angle transition 116, the location of maximum slope shifts toward a slightly larger effective index, which corresponds to the lowest material index near the bottom of the spike region R1.

In a similar way, a guided mode with an effective index only slightly above the critical index may cause the intensity in the vicinity of the critical angle transition 116 to change due to the nonzero breadth of the coupling resonance for the mode. The nonzero breadth may be a result of several factors, including the coupling strength, the resolution of the optical system in the prism-coupling system 28, and aberrations caused by warp of the IOX article 10 in the measurement area.

In each of the above cases, the apparent location of the critical angle in the measured mode spectrum 113TM or 113TE is shifted significantly when the location of the corresponding resonance (bound-mode or leaky-mode resonance) is within a distance from the critical angle that is about the same as the breadth of the resonance in terms of effective index, or smaller.

Hence, a measured mode spectrum 113TM or 113TE may be considered outside of the preferred measurement window when a guided mode is within 0.5 FWHM, such as within 0.6 FWHM or 0.7 FWHM of the breadth of the guided-mode resonance. Similarly, a measured mode spectrum 113TM or 113TE is considered outside of the preferred measurement window when the lowest-intensity point of a leaky mode is within 0.5 FWHM, such as within 0.6 FWHM or 0.7 FWHM breadth of the leaky-mode resonance.

When the leaky-mode resonance is somewhat farther away from the critical index $n_{crit}$, the resonance is broad and asymmetric, and its FWHM may be challenging to measure and define in industrial measurement conditions. Hence, in some embodiments, a different criterion can be used to identify whether a given leaky mode adversely affects the critical angle transition 116. In one such method, the distance between the lowest-intensity point (the dip location) of the leaky mode and the apparent position of the critical angle transition 116 is considered.

The measured mode spectrum 113TM or 113TE may be considered within the preferred measurement window when the distance between the leaky mode dip location and the apparent location of the transition is smaller than 0.2 times the distance from the apparent critical angle transition to the nearest guided-mode location, or smaller than 0.3, 0.4, or 0.5 times the distance from the apparent critical-angle transition to the nearest guided-mode location. The choice of this distance depends at least in part on the shape of the spike region R1, and may be chosen based on empirical evidence from data collected on multiple IOX articles 10.

In another example, the determination of whether both the TM and TE mode spectra 113TM and 113TE are within a preferred measurement window is based on the relationship between the second derivative of the intensity profile of the nearest mode (fringe) to the critical index and the distance between this nearest mode and the apparent location of the critical angle transition 116. Qualitatively, the same method applies for analyzing this relationship for a bound mode and for a leaky mode, except that the decision threshold for a bound mode need not be the same as for a leaky mode.

In some embodiments, the distance between the offending mode and the apparent critical-angle transition 116 is compared to a numerical factor divided by the square root of the second derivative of the optical intensity at the mode location. This is based on the observation that the full width at half-maximum (FWHM) for many bell-shaped intensity distributions of resonant peaks of unit peak value is proportional to the inverse of the square root of the second derivative of the intensity at the location of the resonance (at the minimum for an intensity dip or at the maximum for an intensity peak).

For example, for a Lorentzian of unit peak value, the FWHM is about $$\frac{5.66}{\sqrt{I_1''}},$$

for a Gaussian of unit-peak value it is about $$\frac{2.35}{\sqrt{I_1''}},$$

and for a hyperbolic secant it is about $$\frac{2.63}{\sqrt{I_1''}},$$

where I″ stands for the second derivative of intensity with respect to the horizontal variable of the spectrum (for example, position, angle, effective index, or point number). In many cases, the apparent position of the critical-angle transition 116 is substantially unaffected by the nearby (nearest) mode if the distance between the transition and the nearby mode is larger than about 1.8 times the FWHM breadth of the resonance of the nearby mode.

In some embodiments, the measured mode spectrum 113TM or 113TE is considered outside the preferred measurement window when the distance between the location of a nearby mode and the (apparent) critical-angle transition 116 for the same polarization state is less than 1.8 times the FWHM breadth of the coupling resonance of the nearby mode.

In some embodiments, measured mode spectrum 113TM or 113TE is considered outside the preferred measurement window if it is within less than 1.5 times the FWHM breadth of the coupling resonance of said nearby mode, such as less than 1.2 times the FWHM breadth of the coupling resonance of said nearby mode, less than 1 times the FWHM breadth of the coupling resonance of said nearby mode, less than 0.8 times the FWHM breadth of the coupling resonance of said nearby mode, less than 0.6 times the FWHM breadth of the coupling resonance of said nearby mode, or less than 0.5 times the FWHM breadth of the coupling resonance of said nearby mode.

A preferred threshold ratio for the determining whether a measured mode spectrum 113TM or 113TE is inside or outside a preferred measurement window can be based on a trade-off between the importance of high precision for the measurement of the given stress parameter (e.g., knee stress $CS_k$) and the importance of having a broad measurement window. Greater importance on measurement accuracy favors a larger ratio of the minimum acceptable spacing to the FWHM, and vice versa.

In addition, in cases where the shape of the intensity distribution corresponding to the given mode is well-described by a Lorentzian profile, a preferred threshold value of the ratio maybe higher, such as in the range of 0.8 to 1.8. In cases where the given mode is well-described by a Gaussian profile, the preferred threshold value of the ratio may be lower, such as in the range of 0.5 to 1.2.

Based on the above considerations, a measured mode spectrum 133TM or 113TE is deemed outside the preferred measurement window when the distance between the apparent position of the critical-angle transition 116 and the nearby offending mode is less than or equal to about $$\frac{10.2}{\sqrt{I_1''}}.$$

This is a relatively strict criterion used to ensure at most a negligible shift in the apparent position of the critical-angle transition 116. In various cases, of different line shapes and preferred trade-off between the target accuracy of the stress parameter in question (e.g., knee stress $CS_k$) and breadth of the preferred measurement window, a less-strict threshold for the spacing maybe chosen. For example, the spacing may be less than or equal to a factor of 8.5 times $$\frac{1}{\sqrt{I''}},$$

such as less than or equal to a factor of 6.8 times $$\frac{1}{\sqrt{I''}},$$

5.7 times $$\frac{1}{\sqrt{I''}},$$

4.5 times $$\frac{1}{\sqrt{I''}},$$

3.4 time $1/\sqrt{I''}$, or 2.8 times $$\frac{1}{\sqrt{I_1''}}.$$

Furthermore, in some cases where the shape of the nearby mode resonance is far from Lorentzian, and closer to Gaussian, and a maximized breadth of the measurement window is a higher priority, the preferred threshold value of the spacing between the mode and the apparent transition position 116 may be less than or equal to 2.4 times $$\frac{1}{\sqrt{I''}},$$

such as less than or equal to 1.9 times $$\frac{1}{\sqrt{I''}},$$

1.4 times $$\frac{1}{\sqrt{I''}},$$

or 1.2 times $$\frac{1}{\sqrt{I_1''}}.$$

The second derivative at the location of the nearby mode may be found by smoothing of the signal by low-pass filtering, finding a first derivative digitally and smoothing it by low-pass filtering, then finding a second derivative digitally, smoothing it, and taking the value at the location of the mode resonance. In some embodiments, the second derivative may be found by fitting a parabola (second-order polynomial) to the signal in the closest vicinity of the mode location, and taking the second derivative of the fitting parabola to serve as the second derivative representing the coupling resonance of the mode. Such methods for finding the second derivative are known in the art.

Furthermore, in some embodiments, the intensity distribution in the vicinity of a mode resonance (guided or leaky mode) is normalized so that the minimum intensity corresponds to 0 and the maximum intensity corresponds to 1, or vice versa. In one example of a reflection mode spectrum where the maximum coupling on resonance with a guided or leaky mode corresponds to a local minimum in the reflected intensity, the minimum intensity at the bottom of the reflected-intensity dip may be subtracted from the entire intensity distribution so that a second intensity distribution has a minimum at 0. Then the second intensity distribution is multiplied by a scaling factor so that the maximum value in the vicinity of the local minimum becomes equal to 1. This provides a scaled normalized intensity distribution having a range from 0 to 1. The second-derivative may then be calculated after the normalization procedure.

If it is found that both of the measured TM and TE mode spectra 113TM and 113TE are in the preferred measurement window, then the knee stress $CS_K$ and related parameters (e.g., depth of spike D1, depth of layer DOL, etc.) can be determined. Furthermore, if the TM mode spectrum 113TM is found to be within the preferred measurement window, it may be chosen to calculate the depth of layer DOL based on the TM fringe count only before deciding whether to determine the knee stress $CS_k$ using the same TM mode spectrum and the associated TE spectrum 113TE that was measured at the same time.

If it is found that one of the measured TM and TE mode spectra 113TM or 113TE resides outside of the preferred measurement window, then another (second) pair of TM and TE mode spectra 113TM or 113TE is considered. The second pair of mode spectra 113TM and 113TE may be collected after the determination was made that the at least one of the first TM and TE spectrum was not inside the preferred measurement window. Alternatively, the second pair second pair of mode spectra 113TM and 113TE can be collected in advance using the prism-coupling system 28 set to different measurement conditions than used in obtaining the first pair of mode spectra.

In an example, the light source 60 of the prism-coupling system 28 is adjusted so that the light 62 has a different wavelength for the second measurement than the first measurement. The second wavelength may be chosen to provide continuity of the preferred measurement window so that as an IOX article 10 that falls barely outside the preferred measurement window for the first wavelength falls inside the preferred measurement window for the second spectrum having a different wavelength.

For example, consider the IOX article formed from a Li-containing aluminosilicate glass-based substrate 20 and with a spike region R1 formed using a K+ IOX process. The measured mode spectrum 113TM or 113TE has full mode count between about 2.1 and about 3 fringes at a first measurement wavelength of 590 nm. The calculated surface compressive stress is the range of 500 to 900 MPa.

This particular example IOX article 10 can benefit from a second measurement of the mode spectra 113TM and 113TE using a second wavelength that is longer than the first wavelength by between about 1% and 15% to shift the fringe count range inside a preferred process (measurement) window having a range on the full mode count of 2.3 to 2.7.

Similarly, when a measured mode spectra 113TM or 113TE yield a mode count is just below the lower end of the preferred measurement window (for the present case, when the fringe count falls in the range 1.75-2.1 fringes), then the second wavelength may be made shorter by between about 1% and 25%, depending on how far the mode fringe count falls outside the preferred measurement window.

A more significant shift of the preferred measurement window can be used making by a larger wavelength shift, such as by 18%, 25%, or 30%. A larger shift in the measurement wavelength can be used to establish a larger measurement window by combining the measurement windows of two different measurement wavelengths.

In an example a condition where a spike requires a wavelength that is between two neighboring measurement wavelengths to fall inside the preferred measurement window is avoided. In an example, for a spike having a linear shape with surface index increment Δn above the base index n, the relationship between the fringe count N, the measurement wavelength λ, and the spike depth D1 or $DOL_{sp}$ is:

$$N \approx 3.77\sqrt{n\Delta n}\frac{DOL_{sp}}{\lambda} + 0.25$$

The difference in fringe count between the TM and the TE mode spectrum 113TM and 113TE depends on the difference in Δn between the two mode spectra, since the other parameters that determine the fringe count are the same for the two polarization states in the measurement. If the surface compressive stress is labeled CS, and the knee stress is $CS_k$, then the difference in Δn between the two polarizations is approximately equal to $(CS-CS_k)/SOC$, where SOC is the stress-optic coefficient. The SOC is typically within 15% of $3\times10^{-6}$ RIU/MPa for most chemically strengthened glasses, where RIU stands for refractive-index units.

For a spike produced by an IOX process using K in a Na-based or Li-based glass substrate 20, the difference in Δn between TM and TE is usually about 1/5.6 of the average of the two Δn values. If the stress-induced birefringence of Δn is labeled $\delta n^{TM-TE}$, then the difference in fringe count between the two polarizations is:

$$\delta N^{TM-TE} \approx 3.77\frac{DOL_{sp}}{\lambda}\sqrt{n}\left(\sqrt{\Delta n^{TM}} - \sqrt{\Delta n^{TE}}\right)$$

$$\frac{\delta N^{TM-TE}}{N^{TM} - 0.25} \approx \frac{\left(\sqrt{\Delta n^{TM}} - \sqrt{\Delta n^{TE}}\right)}{\sqrt{\Delta n^{TM}}} =$$

$$\frac{1}{\sqrt{\Delta n^{TM}}}\frac{\Delta n^{TM} - \Delta n^{TE}}{\sqrt{\Delta n^{TM}} + \sqrt{\Delta n^{TE}}} \approx \frac{\Delta n^{TM} - \Delta n^{TE}}{2\Delta n^{TM}} \approx \frac{1}{11.2} \approx 0.09.$$

This means that the fringe count for the TE polarization state is typically about 10/11 of the fringe count of the TM polarization state. Therefore, the fringe count for TE is different by:

$$\delta N^{TM-TE} \approx \frac{N^{TM} - 0.25}{11.2} \approx 0.09 N^{TM} - 0.022.$$

The factor of 0.09 relating the mode count difference to the TM mode count will vary slightly with variations in SOC, and is approximately proportional to the square root of the ratio of SOC to $3\times10^{-6}$. For SOC ranging from about $2\times10^{-6}$ to about $4.5\times10^{-6}$ the corresponding factor would vary from about 0.073 to about 0.11.

Having established that a preferred measurement window for each polarization has a fractional part FP of the fringe count between about 0.1 and 0.8, such as between about 0.15 and 0.75, a preferred measurement window for each polarization may span about 0.6 fringes. Given that there is an offset between the TM and the TE fringe count, the effective preferred measurement window for simultaneously having an accurate measurement of the critical index in the TM and the TE polarization is reduced compared to the single-polarization preferred measurement window by the difference in mode count between TM and TE.

In an example for a typical glass with $0.073N^{TM} \leq \delta N^{TM-TE}$ $0.11N^{TM}$, for a TM mode spectrum 113TM having about 2.6 TM fringes 115TM, the preferred measurement window is reduced from about 0.6 fringes for TM polarization alone to 0.6−(0.19 to 0.29)=(0.31 to 0.41) fringes. Similarly, for a target TM mode spectrum 113TM having 3.6 TM fringes 115TM, the preferred measurement window is reduced from about 0.6 to about 0.6−(0.26 to 0.40)=(0.2 to 0.34) fringes. In the former case, the reduction is between about ⅓ and ½, depending on the value of SOC, while in the latter case the reduction is approximately from about ½ to about ⅔ of the single-polarization preferred window. Thus, the offset in fringe count between TM and TE mode spectra 113TM and 113TE substantially reduces the effective breadth of the continuous process window available within a single preferred measurement window.

In some embodiments where the first TM or TE spectrum 113TM or 113 TE measured at a first measurement wavelength fails to fall inside the preferred measurement window, then a mode spectrum measured at a different (second) measurement wavelength is used to position the TM and the TE spectrum inside the preferred measurement window. If the mode spectrum having a larger fringe count (usually the TM spectrum 113TM) has between about 2.75 and 3.15 fringes, then the measurement wavelength may be increased to bring the fringe count for the TM spectrum in the preferred range 2.15-2.75.

To shift the entire uncovered range 2.75-3.15 fringes to the preferred measurement window 2.15-2.75 fringes using a single longer wavelength, it may be preferred that the single longer second wavelength be at least 12% longer than the first measurement wavelength, preferably 14% longer or more.

On the other hand, it may be desirable to ensure continuity of the measurement so that no IOX article that at the first measurement wavelength has between 2.75 and 3.15 fringes in the polarization state with higher fringe count also falls outside the preferred measurement window at the second (longer) wavelength. Thus, for the longer second measurement wavelength, it may be preferred that the fringe count in the other polarization state does not fall out of the preferred measurement window. In the present example, the change in wavelength is used to shift the mode count from the range 2.15-2.75 fringes to below about 2.1 fringes.

In an example, the higher-fringe-count polarization may have 2.6-2.75 fringes at the first wavelength, and the lower-fringe-count polarization may have 2.35-2.55 fringes for a typical glass with SOC of about $$3\times10^{-6}\frac{RIU}{MPa}.$$

Then, for the example with a lower fringe count of 2.35, a wavelength increase beyond 12% would cause said lower fringe count to drop below 2.1, falling out of the preferred measurement window.

On the other hand, for a mode fringe count of 2.55, a wavelength increase of up to 19.6% would retain the corresponding mode spectrum within the extended preferred measurement window of 2.1-2.8 fringes. Hence, for a typical glass substrate, it is preferred that the wavelength change for the second wavelength not exceed 20% of the first wavelength, such as not exceed 12% of the first wavelength.

In some embodiments, it is preferable that a continuous capability of measuring an IOX article 10 inside a preferred measurement window available among the two or more wavelengths instead of gaining the maximum possible extension of the preferred measurement window by covering the entire problematic range of 2.75-3.15 fringes by switching to the longer wavelength. Hence, having a wavelength increase exceeding 12% or 14% of the first wavelength can be desirable but may not be required or strongly preferred. On the other hand, having a wavelength increase below 20% for some glasses or below 12% for most glasses may be strongly preferred to enable continuous availability of a preferred measurement window among a large variety of IOX articles 10 centered around a target measurement spectrum with 2.1-2.8 fringes. There are less common glasses with a SOC that is substantially lower, such as in the range $0.5 \times 10^{-6}$ to $$2 \times 10^{-6} \frac{RIU}{MPa},$$

for which significantly larger wavelength increase is possible without falling out of the preferred measurement window for the polarization having the lower fringe count.

Examples of preferred wavelength changes for 4 different values of the stress-optic coefficient measured in Brewsters, or B $$\left(1B = 10^{-6} \frac{RIU}{MPa}\right)$$

are given in Tables 1 through 4, below. These examples are given for the case where the preferred change is to increase the wavelength because the larger of the two fringe counts is exceeding the upper end of the measurement window. When the smaller fringe count falls below the bottom of the preferred measurement window, the preferred change is to a shorter wavelength, and similar wavelength percentage changes would be preferable as in the examples of Tables 1 through 4.

Table 1 provides the preferred wavelength change for measurement windows with different fringe counts, for a material with a SOC of about 1 B.

TABLE 1

| Preferred window fringes | larger fringe count | SOC (B) | fringe count diff. | min smaller fringe count | smaller fringe count | max wavelength increase % | preferred min smaller fringe count | preferred max wavelength increase % | desirable wavelength increase for maximum measurement window | low count limits max shift? |
|---|---|---|---|---|---|---|---|---|---|---|
| 2-3 | 2.75 | 1 | 0.07 | 2.68 | 2.1 | 31.1 | 2.15 | 27.7 | 16.0 | N |
| 3-4 | 3.75 | 1 | 0.10 | 3.65 | 3.1 | 19.2 | 3.15 | 17.1 | 11.4 | N |
| 4-5 | 4.75 | 1 | 0.13 | 4.62 | 4.1 | 13.4 | 4.15 | 12.0 | 8.9 | N |
| 5-6 | 5.75 | 1 | 0.16 | 5.59 | 5.1 | 10.0 | 5.15 | 8.9 | 7.3 | N |
| 6-7 | 6.75 | 1 | 0.19 | 6.56 | 6.1 | 7.8 | 6.15 | 6.9 | 6.2 | N |
| 7-8 | 7.75 | 1 | 0.22 | 7.53 | 7.1 | 6.2 | 7.15 | 5.5 | 5.3 | N |
| 8-9 | 8.75 | 1 | 0.25 | 8.50 | 8.1 | 5.1 | 8.15 | 4.4 | 4.7 | Y |
| 9-10 | 9.75 | 1 | 0.28 | 9.47 | 9.1 | 4.1 | 9.15 | 3.6 | 4.2 | Y |
| 10-11 | 10.75 | 1 | 0.31 | 10.44 | 10.1 | 3.4 | 10.15 | 2.9 | 3.8 | Y |
| 11-12 | 11.75 | 1 | 0.34 | 11.41 | 11.1 | 2.8 | 11.15 | 2.4 | 3.5 | Y |
| 12-13 | 12.75 | 1 | 0.37 | 12.38 | 12.1 | 2.3 | 12.15 | 1.9 | 3.2 | Y |
| 13-14 | 13.75 | 1 | 0.40 | 13.35 | 13.1 | 1.9 | 13.15 | 1.5 | 3.0 | Y |

Table 2 provides the preferred wavelength change for measurement windows with different fringe counts, for a material with SOC of about 2 B.

TABLE 2

| Preferred window fringes | larger fringe count | SOC (B) | fringe count diff. | min smaller fringe count | smaller fringe count | max wavelength increase % | preferred min smaller fringe count | preferred max wavelength increase % | desirable wavelength increase for maximum measurement window | low count limits max shift? |
|---|---|---|---|---|---|---|---|---|---|---|
| 2-3 | 2.75 | 2 | 0.15 | 2.60 | 2.1 | 27.1 | 2.15 | 23.7 | 16.0 | N |
| 3-4 | 3.75 | 2 | 0.21 | 3.54 | 3.1 | 15.5 | 3.15 | 13.5 | 11.4 | N |
| 4-5 | 4.75 | 2 | 0.27 | 4.48 | 4.1 | 9.9 | 4.15 | 8.5 | 8.9 | Y |
| 5-6 | 5.75 | 2 | 0.33 | 5.42 | 5.1 | 6.7 | 5.15 | 5.6 | 7.3 | Y |
| 6-7 | 6.75 | 2 | 0.39 | 6.36 | 6.1 | 4.5 | 6.15 | 3.6 | 6.2 | Y |
| 7-8 | 7.75 | 2 | 0.45 | 7.30 | 7.1 | 3.0 | 7.15 | 2.2 | 5.3 | Y |
| 8-9 | 8.75 | 2 | 0.51 | 8.24 | 8.1 | 1.8 | 8.15 | 1.2 | 4.7 | Y |
| 9-10 | 9.75 | 2 | 0.57 | 9.18 | 9.1 | 1.0 | 9.15 | 0.4 | 4.2 | Y |

Table 3 provides the preferred wavelength change for measurement windows with different fringe counts, for a material with SOC of about 3 B.

TABLE 3

| Preferred window fringes | larger fringe count | SOC (B) | fringe count diff. | smaller fringe count | min smaller fringe count | max wavelength increase % | preferred min smaller fringe count | preferred max wavelength increase % | desirable wavelength increase for maximum measurement window | low count limits max shift? |
|---|---|---|---|---|---|---|---|---|---|---|
| 2-3 | 2.75 | 3 | 0.22 | 2.53 | 2.1 | 23.1 | 2.15 | 19.8 | 16.0 | N |
| 3-4 | 3.75 | 3 | 0.31 | 3.44 | 3.1 | 11.8 | 3.15 | 9.9 | 11.4 | Y |
| 4-5 | 4.75 | 3 | 0.40 | 4.35 | 4.1 | 6.4 | 4.15 | 5.1 | 8.9 | Y |
| 5-6 | 5.75 | 3 | 0.49 | 5.26 | 5.1 | 3.3 | 5.15 | 2.2 | 7.3 | Y |
| 6-7 | 6.75 | 3 | 0.58 | 6.17 | 6.1 | 1.2 | 6.15 | 0.3 | 6.2 | Y |

Table 4 provides the preferred wavelength change for measurement windows with different fringe counts, for a material with SOC of about 4 B.

TABLE 4

| Preferred window fringes | larger fringe count | SOC (B) | fringe count diff. | smaller fringe count | min smaller fringe count | max wavelength increase % | preferred min smaller fringe count | preferred max wavelength increase % | desirable wavelength increase for maximum measurement window | low count limits max shift? |
|---|---|---|---|---|---|---|---|---|---|---|
| 2-3 | 2.75 | 4 | 0.30 | 2.45 | 2.1 | 19.0 | 2.15 | 15.9 | 16.0 | N |
| 3-4 | 3.75 | 4 | 0.42 | 3.33 | 3.1 | 8.2 | 3.15 | 6.3 | 11.4 | Y |
| 4-5 | 4.75 | 4 | 0.54 | 4.21 | 4.1 | 3.0 | 4.15 | 1.6 | 8.9 | Y |

The examples in Tables 1 through 4 demonstrate that in some cases it can be advantageous to change the wavelength up to about 28% of the first measurement wavelength. In many cases, the main benefits can be obtained with significantly smaller wavelength changes, e.g., in the range of 8-24%. Mode spectra containing more fringes per polarization state require smaller wavelength shifts to achieve simultaneous preferred-window condition for both wavelengths. For such cases, several discrete wavelengths (3 or more) may be required to provide a wide enough fabrication window with continuous accurate quality control measurement coverage.

Example IOX Article

In one example, an IOX article 10 was formed from a glass substrate 20 having the composition 63.16 mol % $SiO_2$, 2.37 mol % $B_2O_3$, 15.05 mol % $Al_2O_3$, 9.24 mol % $Na_2O$, 5.88 mol % $Li_2O$, 1.18 mol % ZnO, 0.05 mol % $SnO_2$, and 2.47 mol % $P_2O_5$, and a SOC of about 3B. A DIOX process for chemical strengthening was employed. After a first K+-Li+ IOX step (i.e. with K+ as the in-diffusing ion I1), the TM and TE mode spectra 115TM and 115TE each had between 2 and 3 fringes at a first measurement wavelength λ=590 nm. After a second IOX step, the TM and TE mode spectra 115TM and 115TE each had between 3 and 4 fringes at 590 nm. The surface stress CS associated with the formation of the K+-based spike region R1 is usually in the range 500 to 640 MPa. The surface stress CS after the second IOX step using Na+ as the in-diffusing ion I2 is typically in the range 750-950 MPa.

Using the methods described herein, the measurement requirements for both step 1 and step 2 can be fully met with a continuous effective preferred measurement window when using three measurement wavelength windows centered around the measurement wavelengths λ of 545 nm, 590 nm, and 640 nm, respectively. Furthermore, in an example it is preferred that the spectral bandwidth of the measurement light 62 not exceed about 8 nm, 9 nm, and 10 nm, respectively, at these measurement wavelengths. For even higher fringe contrast, the spectral bandwidths can be limited to 4 nm, 5 nm, and 6 nm, respectively. Thus, in one example, each measurement wavelength has a spectral band of 10 nm or less, or in another example, of 6 nm or less.

When the fringe count is close to either the edge of the 590 nm measurement window after step 2, the mode spectrum is brought back inside the preferred measurement window by either increasing or decreasing the measurement wavelength, depending on whether the upper or the lower end of the measurement window approaches at 590 nm. In another example using a three measurement wavelength implementation, the shortest measurement wavelength is about 540 nm, the middle measurement wavelength is about 595 nm, and the longest measurement wavelength is about 650 nm.

While two or three measurement wavelengths have been discussed above by way of example, any reasonable number of measurement wavelengths may be used. For example, using two measurement wavelengths can increase the measurement window by up to a factor of 2, and may be quite adequate to satisfy the needs for a reasonable fabrication process window. On the other hand, in some cases where the spike depth D1 is relatively is large and produces several (e.g., 3, 4, or more) fringes per polarization state, or when the SOC is very high such as 4 B, more than three wavelengths may be preferred. The multiple measurement wavelengths can be positioned closer together than in the three wavelength examples above, e.g., spaced by 7.6% and 9.2%, respectively, of the average wavelength which in these examples is the middle of the three measurement wavelengths.

An exemplary method suppresses systematic errors in the measurement of the knee stress $CS_k$ and in the measurement of the depth of the spike $DOL_{sp}$. The suppression of systematic errors may be essentially complete when the multiple measurement wavelengths are carefully chosen to be close enough to allow a seamless transition between preferred measurement windows at the different wavelengths. This means that the preferred measurement windows at neighboring wavelengths can overlap at least slightly.

The examples listed in Tables 1 through 4 allow selecting preferable wavelength shifts that guarantee such overlap and measurements that are substantially free of systematic errors for a range of samples that may cover a continuous range of fabrication conditions. On the other hand, when the wavelengths are spaced slightly more than the preferred spacing that guarantees window overlap, a maximum expansion of measurement capability is obtained, but at the expense of only partial suppressing systematic errors. The possibility still exists that certain IOX articles 10 can show deviations from accurate measurement, even though the probability of having such samples decreases due to the much increased coverage of the production range with multiple preferred measurement windows.

In some embodiments, the corrective action taken when at least one of the TM and TE spectra 113TM and 113TE is/are not in the preferred measurement window includes changing the thickness of the interfacing fluid 52 (e.g., index oil) to help bring the problematic spectrum inside a preferred measurement window. This is possible because the interfacing fluid can be considered part of the waveguide 26. The main problem that is solved with this corrective action is to determine the knee stress $CS_k$ correctly, i.e., to within select tolerance. The preferred refractive index of the interfacing fluid 52 at the measurement wavelength is higher than the critical index for the polarization state in which the problematic spectrum occurs. Furthermore, the preferred refractive index of the interfacing fluid 52 is higher than the critical index by no more than 0.1, such as by no more than about 0.06, or by no more than 0.04. In some embodiments, the interfacing fluid 52 can be selected to have a refractive index as close as possible to the expected refractive index on the surface of the glass (e.g., the surface refractive index of the potassium spike).

In particular, the interfacing fluid refractive index $n_f$ may be within about 0.004 or 0.003 of the surface refractive index $n_0$. The surface refractive index no is usually different for TM and TE polarizations due to the significant surface stress in the spike, but the difference is usually less than 0.004, and most often less than 0.003. As noted above, the interfacing fluid 52 resides between the prism coupling surface 44 of the coupling prism 40 and the surface 12 of the IOX article 10, and the thickness TH of the interfacing fluid can be controlled using the vacuum system 56. Initially, the amount vacuum can be relatively high, making the thickness TH of the interfacing fluid 52 relatively small, e.g., 200 nm or less, or even 100 nm or less. With this thickness TH of the interfacing fluid 52, the surface compressive stress CS and the spike depth D1 can be measured with adequate accuracy. The spike depth D1 may be over-estimated by as much as 0.1 microns, or even 0.2 microns, which may be acceptable in many cases. The surface compressive stress CS may be slightly under-estimated by assuming that the interfacing fluid thickness is 0 when in fact it might be as high as 0.1 or even 0.2 microns.

In an example, the thickness TH of the interfacing fluid 52 is adjusted in a way that it increases the effective index of a leaky mode to turn it to a quasi-guided mode of the waveguide 26, wherein a quasi-guided mode has an effective index higher than that of the index corresponding to the critical-angle transition.

In another example, thickness TH of the interfacing fluid 52 is adjusted in a way that increases the effective index of a leaky mode to turn it to a quasi-guided mode the waveguide 26 so that fractional part FP of the new mode count now falls in the preferred (extended) measurement window MWE, wherein the refractive index of the interfacing fluid may be higher than the refractive index corresponding to the critical angle.

In another example, the thickness TH of the interfacing fluid 52 is adjusted to decrease the effective index of a leaky mode to turn it into a quasi-guided mode of the waveguide 26 so that fractional part FP of the new mode (fringe) count now falls in the preferred measurement window MWE. In this case, the index of the interfacing fluid 52 may be lower than the index corresponding to said critical angle.

Another example includes changing the refractive of the interfacing fluid 52 to change the effective index of the leaky mode to turn it to a quasi-guided mode having an effective index higher than the critical-angle effective index. The example can also include changing the fractional part FP of the fringe count so that the fractional part FP falls within a fractional-part range associated with the preferred measurement window. In the description herein, changing the refractive index of the interfacing fluid 52 includes replacing at least a portion of a first interfacing fluid having a first refractive index with a second interfacing fluid having a second refractive index. This process can be used to define essentially any refractive index between the first refractive index and the second refractive index.

Once the prism-coupling system 28 is placed in the desired configuration and the mode spectrum 114 collected, the CS and DOL values are then recorded. If both the TM and the TE mode spectra 113TM and 113TE fall within in the preferred measurement window as described above, then the TM and TE critical index $n_{crit}$ is measured by the location of the highest slope in the intensity profiles of the respective critical angle transitions 116. This provides a measure of the birefringence, which is used to calculate the knee stress $CS_k$.

On the other hand, if at least one of the TM or TE mode spectra 115TM and 115TE is not in the preferred measurement window, then a leaky or a guided mode in the problematic TM or TE mode spectrum may be offending, i.e., has an effective index too close to the critical index and adversely affects the apparent location of the critical-angle transition 116. At this point, the thickness TH of the interfacing fluid 52 can be increased, e.g., by decreasing the vacuum (e.g., increasing the pressure) until the effective index of the problematic leaky or guided mode increases enough to be non-offending, i.e., becomes far enough above the critical index that the critical-angle transition 116 is substantially undisturbed and the critical angle (and hence the critical index) for the given polarization can be accurately measured.

It would be preferred that the critical angles for both the TM and TE polarizations be measured at the same time, but this is not required. If the first measured mode spectrum for the other polarization state was in the preferred measurement window before taking the corrective action, it is possible to measure the $CS_k$ by using the measured critical-angle position for the other polarization state using the original thickness of the index-matching fluid 52. Choosing to take both measurements of the TM and TE mode spectra 113TM and 113 TE at the same time helps avoid errors from slight changes in the prism-coupling system 28 that can occur over time.

Experimental Results

Figure 4:
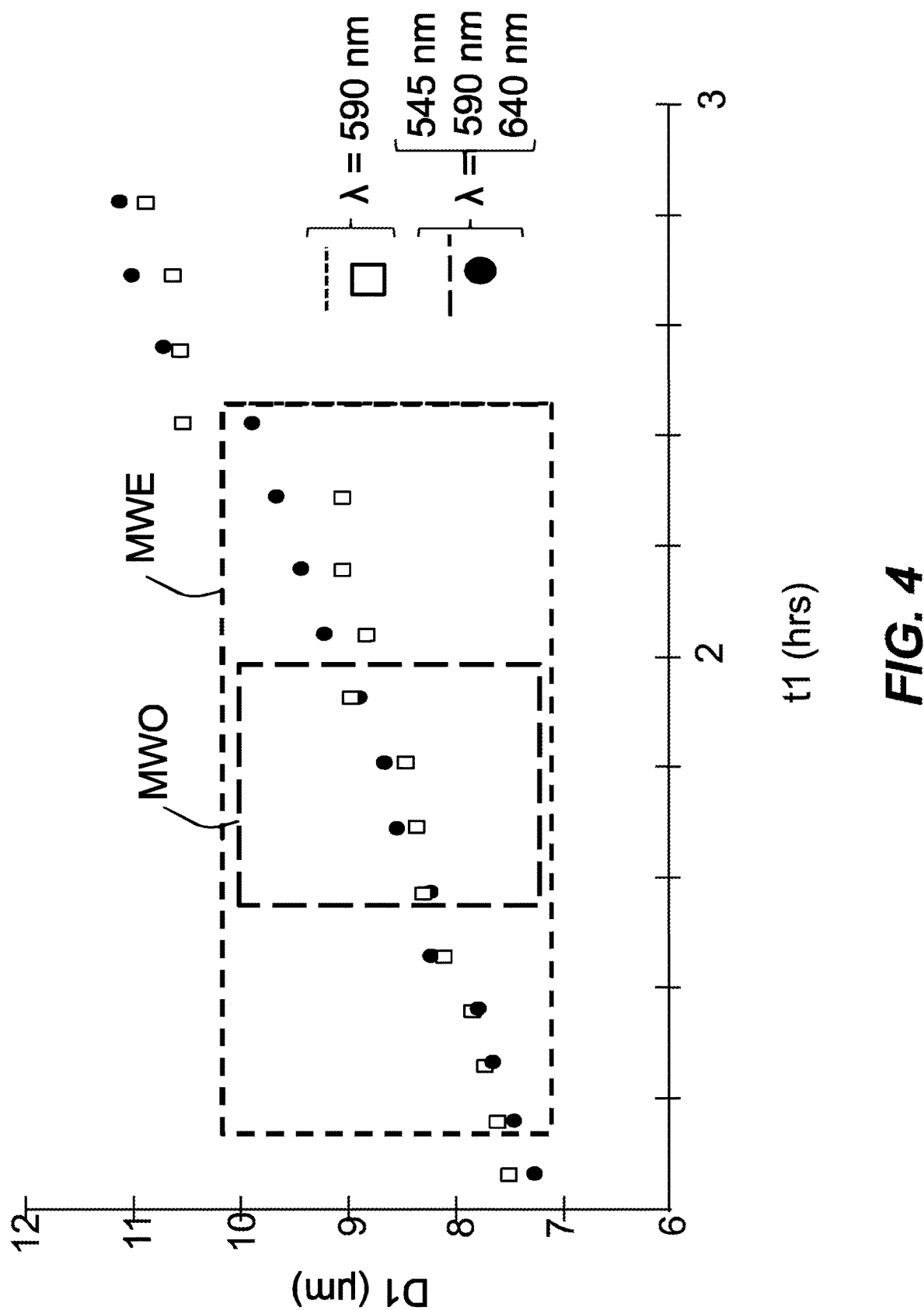
FIG. 4 is a plot of the measured spike depth $DOL_{sp}$ (µm) versus the "step 1" diffusion time t1 (s) for example IOX articles formed from a lithium-containing aluminosilicate glass substrate using a DIOX process, with the measurements performed by a single-wavelength prism-coupling system (open squares) and a three-wavelength prism-coupling system (dark circles), and wherein the "step 1" diffusion time t1 is for the first step of the two-step DIOX process.

FIG. 4 is a plot of the spike depth D1 (μm) versus time t1 (hours) for a first IOX process for an IOX article 10 made using a lithium-based aluminosilicate glass substrate 20. The open squares are measurements made using the prism-coupling system 28 with a light source 60 operating at a single measurement wavelength λ of 595 nm. The dark circles are measurements with the prism-coupling system 28 with a light source 60 configured to operate at three different measurement wavelengths λ centered at 540 nm, 595 nm, and 650 nm.

An initial ("original") measurement window MWO for the single-wavelength measurement method is depicted with long-dash lines, while an extended (preferred) measurement window MWE for the three-wavelength measurement methods and prism-coupling systems as described herein is shown with short-dash lines. The extended measurement window MWE that uses three measurement wavelengths λ is significantly extended as compared to the single-wavelength measurement window MWO. Since the IOX process time defines the refractive index profile of the IOX article 10, an extended measurement window MWE having a wider range of IOX process times means IOX articles with a larger range of spike-based refractive index profiles can be characterized for at least one stress characteristic such as the knee stress $CS_k$.

Figure 5:
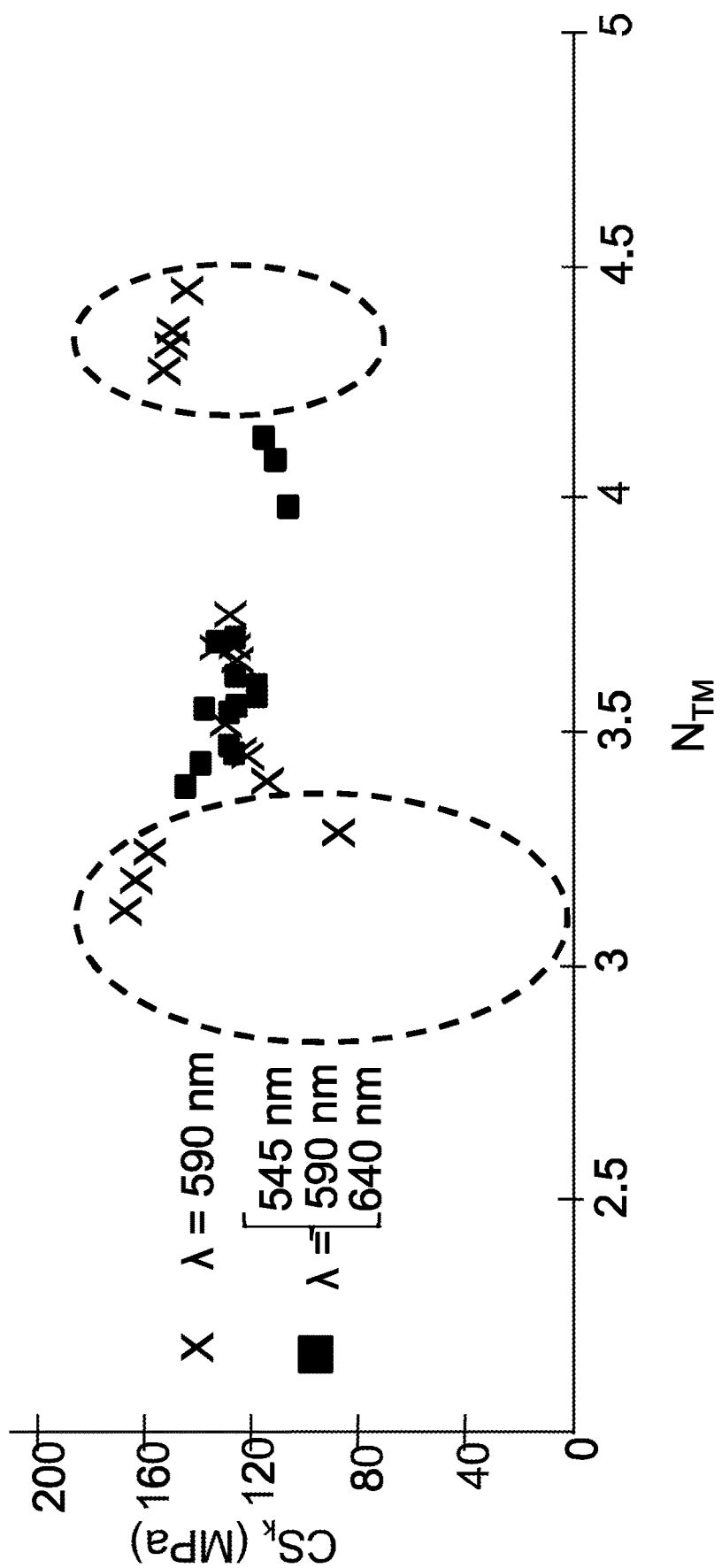
FIG. 5 is a plot of the measured knee stress $CS_k$ (MPa) versus the TM fringe (mode) count $N_{TM}$ based on the measurements made on example IOX articles formed from lithium-containing aluminosilicate glass substrates and using a same DIOX process where the step 1 diffusion time t1 was the same but the step 2 diffusion time was varied for the different IOX articles, with the single-wavelength measurements shown by open squares and a three-wavelength measurements shown by dark circles.

FIG. 5 is a plot of the knee stress $CS_k$ (MPa) versus the TM mode (fringe) count $N_{TM}$ for example IOX articles 10 formed from lithium-containing aluminosilicate glass substrates 20. The single-wavelength measurements were made at a measurement wavelength λ of 595 nm and are represented by λ's. Three-wavelength measurements were made at measurement wavelengths of 540 nm, 595 nm, 650 nm and are represented by dark squares. The single-wavelength measurements do not follow a monotonic continuous decrease of $CS_k$ with increased mode count, while the three-wavelength measurements follow such a pattern within a precision limited by a relatively small measurement noise not exceeding 20 MPa. The increase in mode count was obtained with a two-step IOX process, where step 1 was the same for all samples, and in step 2 the diffusion time was varied between different samples, all using the same step 2 IOX bath. The TM mode (fringe) count varies between about 3 and about 4.5 modes in this data set. The TE mode count is lower than the TM mode count by about 9% (0.3-0.4 fringes) for the same data set and is outside the extended measurement window for the encircled data points.

Figure 6:
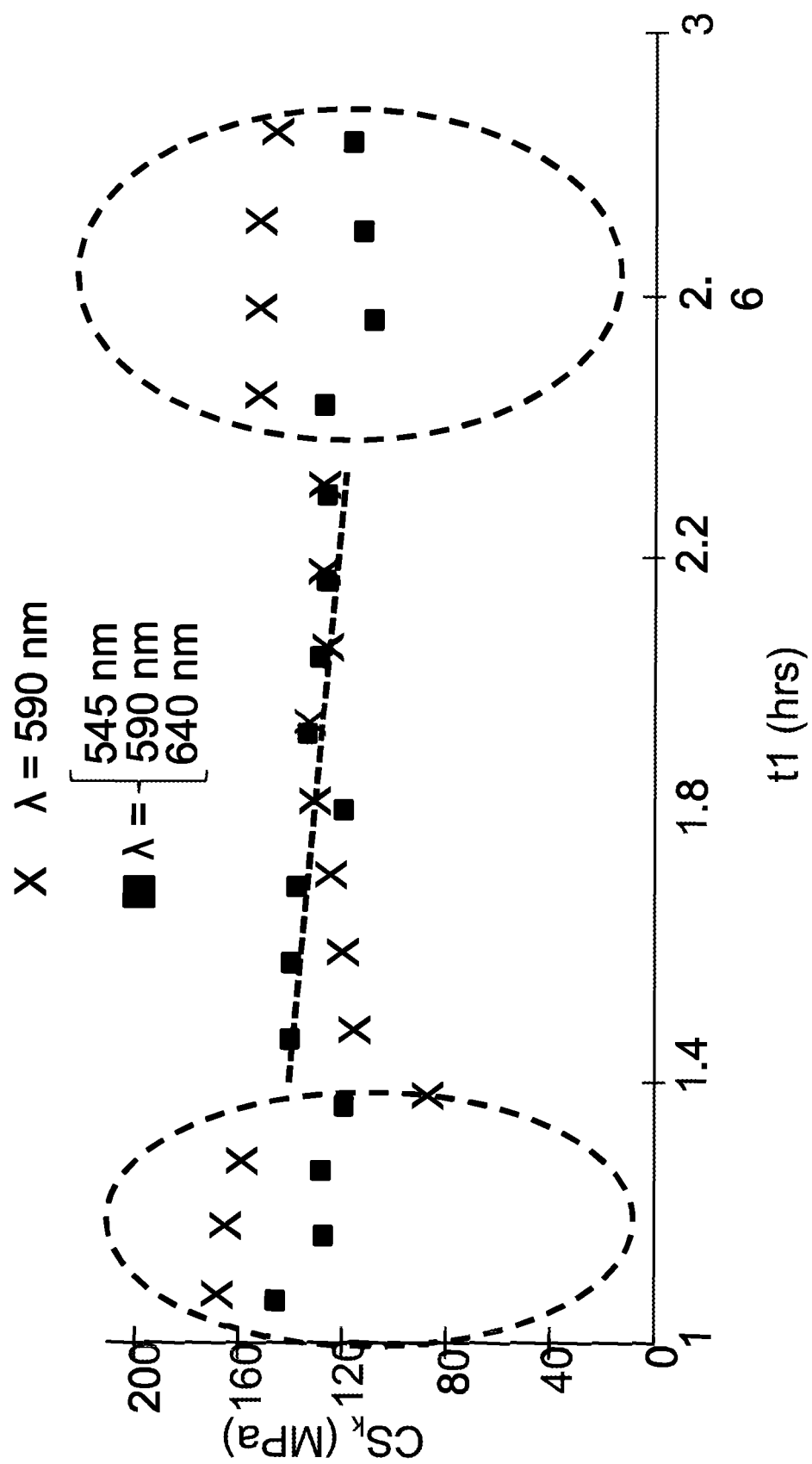
FIG. 6 is a plot of the measured knee stress $CS_k$ (MPa) after the two-step ion exchange (DIOX) versus the first-step ion-exchange time ("step 1 time") t1 (hours) for the same type of IOX articles as considered in FIG. 4.

FIG. 6 plots the measured knee stress $CS_k$ after the two-step ion exchange (DIOX) versus the first-step ion-exchange time ("step 1 time) t1 (hours) for the same IOX articles 10 measured in FIG. 5. The expected trend of $CS_k$ is a slow monotonic decrease with increasing time t1. The single-wavelength (λ=595 nm) measurements are shown with λ-symbols, while the three-wavelength (λ=540 nm, 595 nm and 650 nm) measurement results are shown as dark squares. Even though the three wavelengths are somewhat farther apart than optimum for continuous coverage, the data points for the three-wavelength measurements better hew to the expected monotonic trend (dashed line) than the single-wavelength measurements. Thus, the prism-coupling system 28 having a light source 60 that emits two or more closely spaced measurement wavelengths (e.g., λ=545 nm, 590 nm, and 640 nm) significantly reduces the deviations from the expected monotonic trend, which translates into more accurate measurement of stress-related characteristics.

Figure 7:
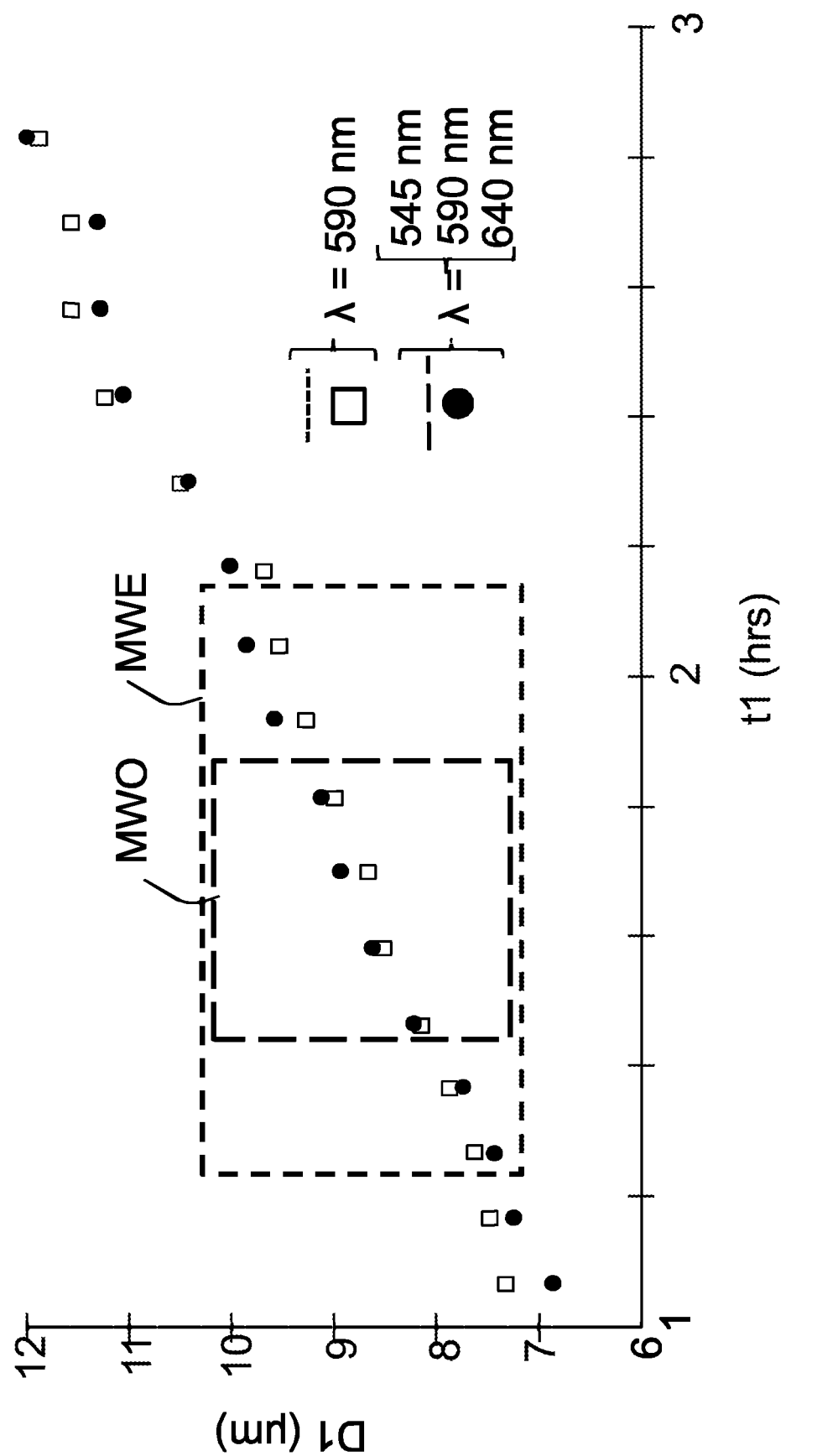
FIG. 7 is a similar plot to that of FIG. 4 for additional example measurements.

FIG. 7 is similar to FIG. 4 and plots the spike depth D1 (microns) versus step 1 time t1 (hours) for the IOX articles 10 of FIG. 6 for measurements made using a single-wavelength prism-coupling system 28 having a single measurement wavelength of 595 nm (open squares), and a prism-coupling system 28 having three measurement wavelengths of 540 nm, 595 nm, and 650 nm (dark circles). The single-wavelength measurement window MWO is shown with long-dash lines, while the extended measurement window MWE is shown with short-dash lines. On the upper right edge of the preferred measurement window the reported spike depth D1 falls below the accurate value due to the proximity of an offending TM leaky mode to the TM critical angle transition 116. Likewise, on the lower left edge of the preferred measurement window, an offending TE guided mode occurs too close to the critical angle transition 116. The knee stress $CS_k$ can be under-estimated even though the spike depth D1 is not affected since the spike depth D1 in the plots is measured based on the TM mode spectrum 113 TM only. A more accurate estimation of the knee stress can be obtained by including data from both the TE and TM mode spectra 113TE and 113TM.

Figure 8A:
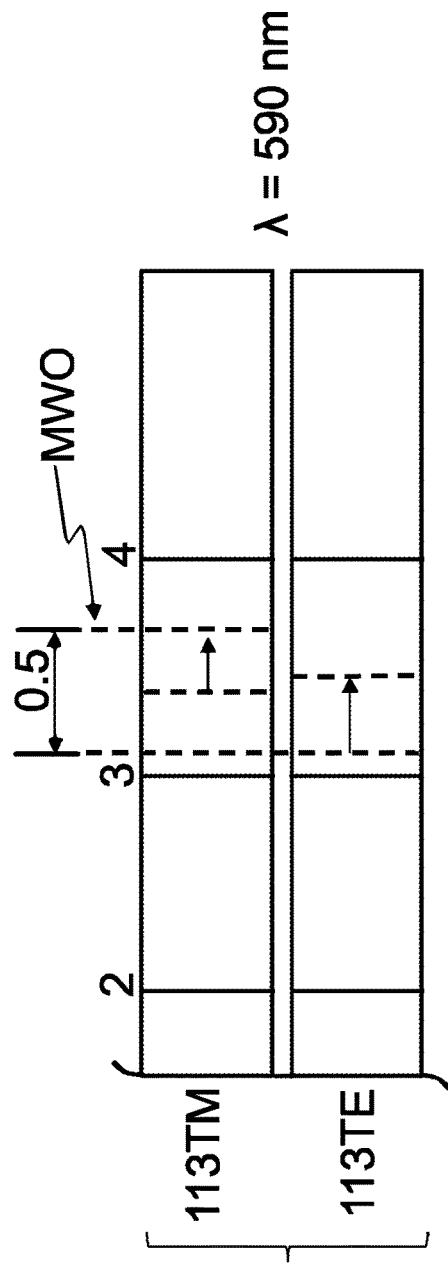
FIG. 8A is a schematic diagram of an example TM and TE mode spectra pair for a single-wavelength measurement and that respectively include four TM and TE modes or fringes, and showing a measurement window size of 0.5 fringes.
Figure 8B:
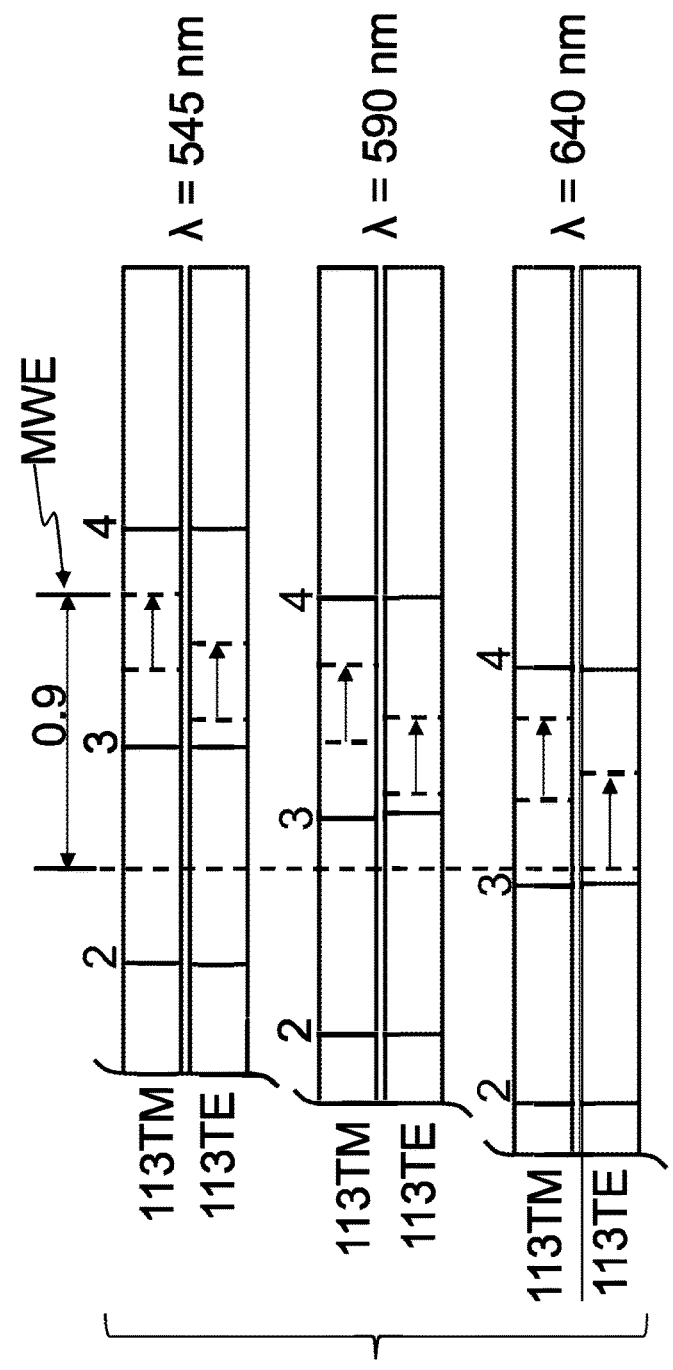
FIG. 8B is similar to FIG. 8A except that it shows three TM and TE mode spectra pairs, one for each of three measurement wavelengths, and shows a larger effective measurement window of about 0.9 fringes, which is almost double that for the single-wavelength case of FIG. 8A.

FIGS. 8A and 8B are schematic diagrams of the TM and TE mode spectra 113TM and 113TE that respectively include four TM and TE modes or fringes 115TM and 115TE. FIG. 8A shows mode spectra 113TM and 113TE for a single measurement wavelength while FIG. 8B shows three pairs of mode spectra 113TM and 113TE, one pair for each of three measurement wavelengths of 545 nm, 590 nm and 640 nm. The effective measurement window MWO for the single-wavelength system of FIG. 8A has a size of about 0.5 fringes while the extended measurement window MWE for the three-wavelength system of FIG. 8B measured is about 0.9 fringes, or about twice that of the single-wavelength measurement window MWO.

Frangibility

Frangible behavior or "frangibility" refers to specific fracture behavior when a glass-based article is subjected to an impact or insult. As utilized herein, a glass-based article (and in particular, a glass-based IOX article 10 such as considered herein) is considered non-frangible when it exhibits at least one of the following in a test area as the result of a frangibility test: (1) four or less fragments with a largest dimension of at least 1 mm, and/or (2) the number of bifurcations is less than or equal to the number of crack branches. The fragments, bifurcations, and crack branches are counted based on any 2 inch by 2 inch square centered on the impact point. Thus, a glass-based article is considered non-frangible if it meets one or both of tests (1) and (2) for any 2 inch by 2 inch square centered on the impact point where the breakage is created according to the procedure described below. In various examples, the chemically strengthened IOX article 10 can be frangible or non-frangible.

In a frangibility test, an impact probe is brought into contact with the glass-based article, with the depth to which the impact probe extends into the glass-based article increasing in successive contact iterations. The step-wise increase in depth of the impact probe allows the flaw produced by the impact probe to reach the tension region while preventing the application of excessive external force that would prevent the accurate determination of the frangible behavior of the glass. In one embodiment, the depth of the impact probe in the glass may increase by about 5 μm in each iteration, with the impact probe being removed from contact with the glass between each iteration. The test area is any 2 inch by 2 inch square centered at the impact point.

Figure 9A:
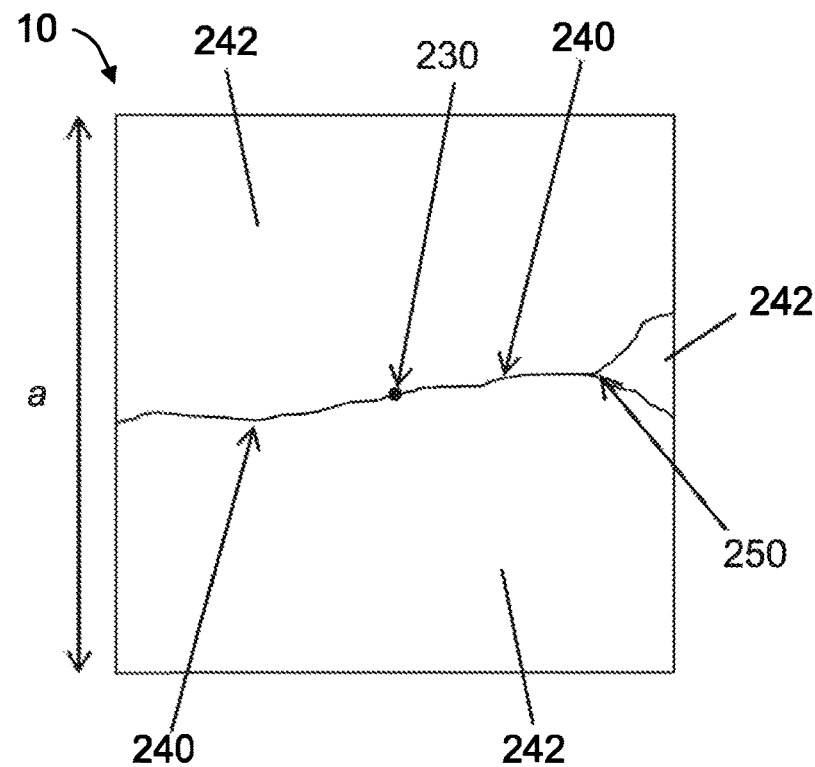
FIG. 9A depicts a non-frangible test result on a test glass-based article in the form of an example IOX article.

FIG. 9A depicts a non-frangible test result on a test glass-based article in the form of an example IOX article 10.

As shown in FIG. 9A, the test area is a square that is centered at the impact point 230, where the length of a side of the square a is 2 inches. The non-frangible sample shown in FIG. 9A includes three fragments 242, and two crack branches 240 and a single bifurcation 250. Thus, the non-frangible IOX article 10 shown in FIG. 9A contains less than 4 fragments having a largest dimension of at least 1 mm and the number of bifurcations is less than or equal to the number of crack branches. As utilized herein, a crack branch originates at the impact point, and a fragment is considered to be within the test area if any part of the fragment extends into the test area.

While coatings, adhesive layers, and the like may be used in conjunction with the strengthened glass articles described herein, such external restraints are not used in determining the frangibility or frangible behavior of the glass-based articles. In some embodiments, a film that does not impact the fracture behavior of the glass-based article may be applied to the glass-based article prior to the frangibility test to prevent the ejection of fragments from the glass article, increasing safety for the person performing the test.

Figure 9B:
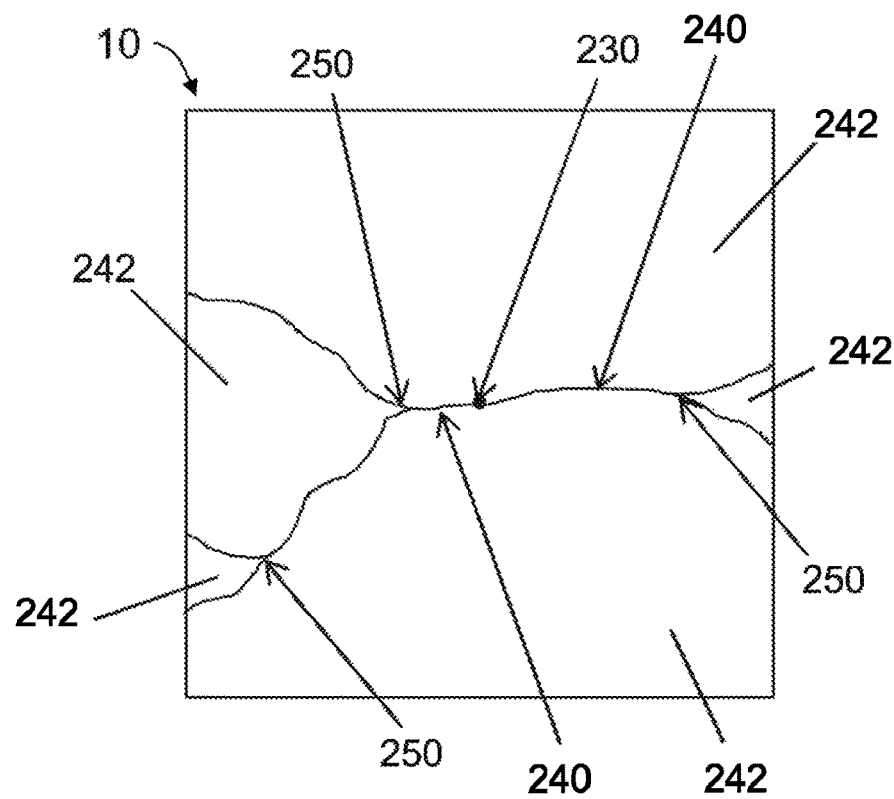
FIG. 9B depicts a frangible test result on a test glass article in the form of an example IOX article.

FIG. 9B depicts a frangible test result on a test glass article in the form of an example IOX article 10. The frangible IOX article 10 includes 5 fragments 242 having a largest dimension of at least 1 mm. The IOX article 10 depicted in FIG. 9B includes 2 crack branches 240 and 3 bifurcations 250, producing more bifurcations than crack branches. Thus, the sample depicted in FIG. 9B does not exhibit either four or less fragments or the number of bifurcations being less than or equal to the number of crack branches.

In the frangibility test described herein, the impact is delivered to the surface of the glass-based article with a force that is just sufficient to release the internally stored energy present within the strengthened glass-based article. That is, the point impact force is sufficient to create at least one new crack at the surface of the strengthened glass-based article and extend the crack through the compressive stress CS region (i.e., depth of layer) into the region that is under central tension CT.

It will be apparent to those skilled in the art that various modifications to the preferred embodiments of the disclosure as described herein can be made without departing from the spirit or scope of the disclosure as defined in the appended claims. Thus, the disclosure covers the modifications and variations provided they come within the scope of the appended claims and the equivalents thereto.

What is claimed is:

1. A method of estimating a knee stress in a chemically strengthened article having a refractive index profile with a near-surface spike region and a deep region that define an optical waveguide in a glass-based substrate, comprising:
    a) using a prism-coupling system set in an initial measurement configuration, collecting a transverse magnetic (TM) and a transverse electric (TE) mode spectra for the chemically strengthened article;
    b) examining the TM and TE mode spectra and finding that they do not fall within a preferred measurement window that can produce an accurate estimate of the knee stress to within a select tolerance;
    c) changing the measurement configuration of the prism-coupling system one or more times and measuring new transverse magnetic (TM) and transverse electric (TE) mode spectra until the new TM and TE mode spectra fall within the preferred measurement window; and
    d) using the new TM and TE mode spectra to determine the knee stress.

2. The method according to claim 1, wherein changing the measurement configuration can include changing at least one of: i) a wavelength of measurement light of the prism-coupler system; ii) a thickness of an interfacing fluid used to provide optical coupling between a coupling prism of the prism-coupler system and the optical waveguide; and iii) a refractive index of the interfacing fluid.

3. The method according to claim 2, wherein the measurement wavelengths can be changed between three different measurement wavelengths that fall within a wavelength range from 540 nm to 650 nm.

4. The method according to claim 2, wherein the changing the measurement wavelength includes changes the measurement wavelength by at least 1%.

5. The method according to claim 4, wherein the changing the measurement wavelength changes the measurement wavelength by between 1% to 25%.

6. The method according to claim 5, wherein the changing the measurement wavelength changes the measurement wavelength by between 2% and 15%.

7. The method according to claim 1, wherein each of the TM and TE mode spectra has a fringe count having an integer part and a fractional part FP, and wherein for the preferred measurement window the fractional part FP for each of the TM and TE mode spectra is between 0.1 and 0.85.

8. The method according to claim 7, wherein for the preferred measurement window the fractional part FP for each of the TM and TE mode spectra is between 0.15 and 0.75.

9. The method according to claim 7, wherein each of the TM and TE mode spectra comprise a critical-angle transition between a total-internal-reflection (TIR) section and a non-TIR section, wherein the TIR section comprising fringes with locations and including a closest fringe located closest the critical-angle transition at a distance $\Delta n_f$ thereto, and further comprising extrapolating the fringe locations into the non-TIR section to define a location of a virtual fringe having a distance DVF from the closest fringe, and determining the fractional part FP via the relationship $FP=\Delta n_f/DVF$.

10. The method according to claim 1, wherein the prism-coupling system comprises a light source comprising multiple light-emitting elements that respectively emit light at different measurement wavelengths, and wherein changing the measurement configuration includes adjusting the measurement wavelength comprising turning off one of the light-emitting elements and turning on another of the light-emitting elements.

11. A prism-coupling system for measuring a stress characteristic of a chemically strengthened ion-exchanged (IOX) article having a near-surface spike region and a deep region formed in a glass-based substrate and that define an optical waveguide, comprising:
    a coupling prism having an input surface, an output surface and a coupling surface, and wherein the coupling, surface interfaces with the waveguide at a substrate upper surface, thereby defining an interface having an interfacing fluid with an interfacing fluid refractive index and a thickness;
    a light source system configured to emit measurement light having a selectable measurement wavelength, wherein the measurement light illuminates the interface through the input surface of the prism, thereby forming reflected light that exits the output surface of the coupling prism, wherein the reflected light defines a transverse magnetic (TM) mode spectrum and a transverse electric (TE) mode spectrum;
a photodetector system arranged to receive the reflected light from the coupling prism and detect an initial TM mode spectrum and an initial TE mode spectrum at an initial measurement wavelength;
a controller configured to perform the acts of:
i) processing the initial TM mode spectrum and the initial TE mode spectrum and finding that at least one of the first TM mode spectrum and the first TE mode spectrum resides outside of a preferred measurement window that allows estimating the knee stress from the first TM mode spectrum and the first TE mode spectrum to within a select tolerance;
ii) changing the measurement wavelength of the light source one or more times to the selectable measurement wavelengths and collecting respective one or more new TM mode spectrums and one or more new TE mode spectrums until the new TM mode spectrum and the new TE mode spectrum reside within the preferred measurement window; and
iii) determining the knee stress to within the select tolerance using the new TM mode spectrum and the TE mode spectrum that reside within the preferred measurement window.

12. The prism-coupling system according to claim 11, wherein the light-source system comprises a tunable laser.

13. The prism-coupling system according to claim 11, wherein the light-source system comprises a plurality of light-emitting elements that each emits one of the selectable measurement wavelengths.

14. The prism-coupling system according to claim 13, wherein the plurality of light-emitting elements comprises at least one of laser diodes or light-emitting diodes.

15. The prism-coupling system according to claim 11, wherein the selectable measurement wavelengths are between 540 nm and 650 nm.

16. The prism-coupling system according to claim 11, wherein the selectable measurement wavelengths comprise three different measurement wavelengths each having a wavelength band of less than 10 nm.

17. The prism-coupling system according to claim 11, wherein the selectable measurement wavelengths comprise three different measurement wavelengths each having a wavelength band of less than 6 nm.

18. The prism-coupling system according to claim 11, wherein the selectable measurement wavelengths differ from each other by at least 1%.

19. The prism-coupling system according to claim 18, wherein the selectable measurement wavelengths differ from each other by between 1% to 25%.

20. The prism-coupling system according to claim 19, wherein different measurement wavelengths differ from each other by between 2% and 15%.

21. The prism-coupling system according to claim 20, wherein the selectable measurement wavelengths differ from each other by between 3% and 11%.

22. The prism-coupling system according to claim 11, wherein each of the TM mode spectrum and the TE mode spectrum has a fringe count having an integer part and a fractional part FP, and wherein for the preferred measurement window the fractional part FP for each of the TM mode spectrum and TE mode spectrum is between 0.1 and 0.85.

23. The prism-coupling system according to claim 22, wherein for the preferred measurement window the fractional part FP for each of the TM and TE mode spectra is between 0.15 and 0.75.

24. The prism-coupling system according to claim 22, wherein each of the TM mode spectrum and the TE mode spectrum comprises a critical-angle transition between a total-internal-reflection (TIR) section and a non-TIR section, wherein the TIR section comprising fringes with locations and including a closest fringe located closest the critical-angle transition at a distance $\Delta n_f$ thereto, and further comprising the controller extrapolating the fringe locations into the non-TIR section to define a location of a virtual fringe having a distance DVF from the closest fringe, and determining the fractional part FP via the relationship $FP = \Delta n_f / DVF$.

* * * * *

UNITED STATES PATENT AND TRADEMARK OFFICE
CERTIFICATE OF CORRECTION

PATENT NO. : 11,169,037 B2
APPLICATION NO. : 16/921107
DATED : November 9, 2021
INVENTOR(S) : Ryan Claude Andrews et al.

Page 1 of 1

It is certified that error appears in the above-identified patent and that said Letters Patent is hereby corrected as shown below:

On the Title Page

Page 2, Column 2, item [56], Line 6, delete "IEE" and insert -- IEEE --, therefor.

Page 2, Column 2, item [56], Line 24, delete "Exhange" and insert -- Exchange --, therefor.

In the Claims

Column 32, Lines 57-58, Claim 11, delete "coupling," and insert -- coupling --, therefor.

Column 33, Line 8, Claim 11, delete "i)" and insert -- iv) --, therefor.

Column 33, Line 15, Claim 11, delete "ii)" and insert -- v) --, therefor.

Column 33, Line 22, Claim 11, delete "iii)" and insert -- vi) --, therefor.

Signed and Sealed this
Thirteenth Day of September, 2022

Katherine Kelly Vidal
*Director of the United States Patent and Trademark Office*